(12) United States Patent
Kiani et al.

(10) Patent No.: US 7,142,901 B2
(45) Date of Patent: Nov. 28, 2006

(54) PARAMETER COMPENSATED PHYSIOLOGICAL MONITOR

(75) Inventors: Massi E. Kiani, Laguna Niguel, CA (US); Mohamed Diab, Mission Viejo, CA (US); Ammar Al-Ali, Tustin, CA (US); Walter M. Weber, Laguna Hills, CA (US)

(73) Assignee: Masimo Corporation, Irvine, CA (US)

( * ) Notice: Subject to any disclaimer, the term of this patent is extended or adjusted under 35 U.S.C. 154(b) by 356 days.

(21) Appl. No.: 10/714,526

(22) Filed: Nov. 14, 2003

(65) Prior Publication Data

US 2004/0242980 A1    Dec. 2, 2004

Related U.S. Application Data

(63) Continuation-in-part of application No. 10/671,179, filed on Sep. 25, 2003.

(60) Provisional application No. 60/426,638, filed on Nov. 16, 2002, provisional application No. 60/413,494, filed on Sep. 25, 2002.

(51) Int. Cl.
    *A61B 5/00* (2006.01)

(52) U.S. Cl. .................. 600/331; 600/322; 600/323

(58) Field of Classification Search ................. 600/322, 600/331, 323, 364
See application file for complete search history.

(56) References Cited

U.S. PATENT DOCUMENTS

| | | | |
|---|---|---|---|
| 4,960,128 A | 10/1990 | Gordon et al. | |
| 5,163,438 A | 11/1992 | Gordon et al. | |
| 5,337,744 A | 8/1994 | Branigan | |
| 5,431,170 A | 7/1995 | Mathews | |
| 5,452,717 A | 9/1995 | Branigan et al. | |
| 5,482,036 A | 1/1996 | Diab et al. | |
| 5,490,505 A | 2/1996 | Diab et al. | |
| 5,494,043 A | 2/1996 | O'Sullivan et al. | |
| 5,533,511 A | 7/1996 | Kaspari et al. | |
| 5,590,649 A | 1/1997 | Caro et al. | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,685,299 A | 11/1997 | Diab et al. | |
| 5,725,480 A * | 3/1998 | Oosta et al. | 600/310 |
| D393,830 S | 4/1998 | Tobler et al. | |
| 5,743,262 A | 4/1998 | Lepper, Jr. et al. | |
| 5,758,644 A | 6/1998 | Diab et al. | |
| 5,760,910 A | 6/1998 | Lepper, Jr. et al. | |
| 5,769,785 A | 6/1998 | Diab et al. | |
| 5,782,757 A | 7/1998 | Diab et al. | |
| 5,785,659 A | 7/1998 | Caro et al. | |
| 5,791,347 A | 8/1998 | Flaherty et al. | |
| 5,810,734 A | 9/1998 | Caro et al. | |
| 5,823,950 A | 10/1998 | Diab et al. | |
| 5,830,131 A | 11/1998 | Caro et al. | |
| 5,833,618 A | 11/1998 | Caro et al. | |
| 5,842,979 A * | 12/1998 | Jarman | 600/322 |

(Continued)

*Primary Examiner*—Eric Winakur
*Assistant Examiner*—Etsub D. Berhanu
(74) *Attorney, Agent, or Firm*—Knobbe Martens Olson & Bear LLP

(57) ABSTRACT

A monitor has a primary input from which a spectral characteristic of a tissue site can be derived. The monitor also has a secondary input from which at least one parameter can be determined. A compensation relationship of the spectral characteristic, the parameter and a compensated physiological measurement is determined. A processor is configured to output the compensated physiological measurement in response to the primary input and the secondary input utilizing the compensation relationship.

13 Claims, 19 Drawing Sheets

U.S. PATENT DOCUMENTS

| | | |
|---|---|---|
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,978,691 A | 11/1999 | Mills |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,104,938 A | 8/2000 | Huiku et al. |
| 6,110,522 A | 8/2000 | Lepper, Jr. et al. |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,236,872 B1 | 5/2001 | Diab et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,334,065 B1 | 12/2001 | Al-Ali et al. |
| 6,349,228 B1 | 2/2002 | Kiani et al. |
| 6,360,114 B1 | 3/2002 | Diab et al. |
| 6,371,921 B1 | 4/2002 | Caro et al. |
| 6,377,829 B1 | 4/2002 | Al-Ali |
| 6,388,240 B1 | 5/2002 | Schulz et al. |
| 6,397,091 B1 | 5/2002 | Diab et al. |
| 6,421,549 B1 * | 7/2002 | Jacques ................. 600/331 |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B1 | 12/2002 | Diab et al. |
| 6,515,273 B1 | 2/2003 | Al-Ali |
| 6,525,386 B1 | 2/2003 | Mills et al. |
| 6,526,300 B1 | 2/2003 | Kiani et al. |
| 6,541,756 B1 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,597,933 B1 | 7/2003 | Kiani et al. |
| 6,606,511 B1 | 8/2003 | Ali et al. |
| 6,632,181 B1 | 10/2003 | Flaherty et al. |
| 6,640,116 B1 | 10/2003 | Diab |
| 6,643,530 B1 | 11/2003 | Diab et al. |
| 6,650,917 B1 | 11/2003 | Diab et al. |
| 6,654,624 B1 | 11/2003 | Diab et al. |
| 6,658,276 B1 | 12/2003 | Kianl et al. |
| 6,671,531 B1 | 12/2003 | Al-Ali et al. |
| 6,678,543 B1 | 1/2004 | Diab et al. |
| 6,684,090 B1 | 1/2004 | Ali et al. |
| 6,697,656 B1 | 2/2004 | Al-Ali |
| 6,697,658 B1 | 2/2004 | Al-Ali |
| RE38,476 E | 3/2004 | Diab et al. |
| 6,699,194 B1 | 3/2004 | Diab et al. |
| 6,714,804 B1 | 3/2004 | Al-Ali et al. |
| RE38,492 E | 4/2004 | Diab et al. |
| 6,725,075 B1 | 4/2004 | Al-Ali |
| 6,745,060 B1 | 6/2004 | Diab et al. |
| 6,760,607 B1 | 7/2004 | Al-Ali |
| 6,770,028 B1 | 8/2004 | Ali et al. |
| 6,771,994 B1 | 8/2004 | Kiani et al. |
| 6,792,300 B1 | 9/2004 | Diab et al. |
| 6,813,511 B1 | 11/2004 | Diab et al. |
| 6,816,741 B1 | 11/2004 | Diab |
| 6,822,564 B1 | 11/2004 | Al-Ali |
| 6,826,419 B1 | 11/2004 | Diab et al. |
| 6,830,711 B1 | 12/2004 | Mills et al. |
| 6,850,787 B1 | 2/2005 | Weber et al. |
| 6,850,788 B1 | 2/2005 | Al-Ali |
| 6,852,083 B1 | 2/2005 | Caro et al. |
| 6,861,639 B1 | 3/2005 | Al-Ali |
| 6,898,452 B1 | 5/2005 | Al-Ali et al. |
| 6,920,345 B1 | 7/2005 | Al-Ali et al. |
| 6,931,268 B1 | 8/2005 | Kiani-Azarbayjany et al. |
| 6,934,570 B1 | 8/2005 | Kiani et al. |
| 6,939,305 B1 | 9/2005 | Flaherty et al. |
| 6,943,348 B1 | 9/2005 | Coffin IV |
| 6,950,687 B1 | 9/2005 | Al-Ali |
| 6,961,598 B1 | 11/2005 | Diab |
| 6,970,792 B1 | 11/2005 | Diab |
| 6,979,812 B1 | 12/2005 | Al-Ali |
| 6,985,764 B1 | 1/2006 | Mason et al. |
| 6,993,371 B1 | 1/2006 | Kiani et al. |
| 6,996,427 B1 | 2/2006 | Ali et al. |
| 6,999,904 B1 | 2/2006 | Weber et al. |
| 7,003,338 B1 | 2/2006 | Weber et al. |
| 7,003,339 B1 | 2/2006 | Diab et al. |
| 7,015,451 B1 | 3/2006 | Dalke et al. |
| 7,024,233 B1 | 4/2006 | Al et al. |
| 7,027,849 B1 | 4/2006 | Al-Ali |
| 7,030,749 B1 | 4/2006 | Al-Ali |
| 7,039,449 B1 | 5/2006 | Al-Ali |
| 7,041,060 B1 | 5/2006 | Flaherty et al. |
| 7,044,918 B1 | 5/2006 | Diab |
| 2002/0133068 A1 | 9/2002 | Huiku |

* cited by examiner

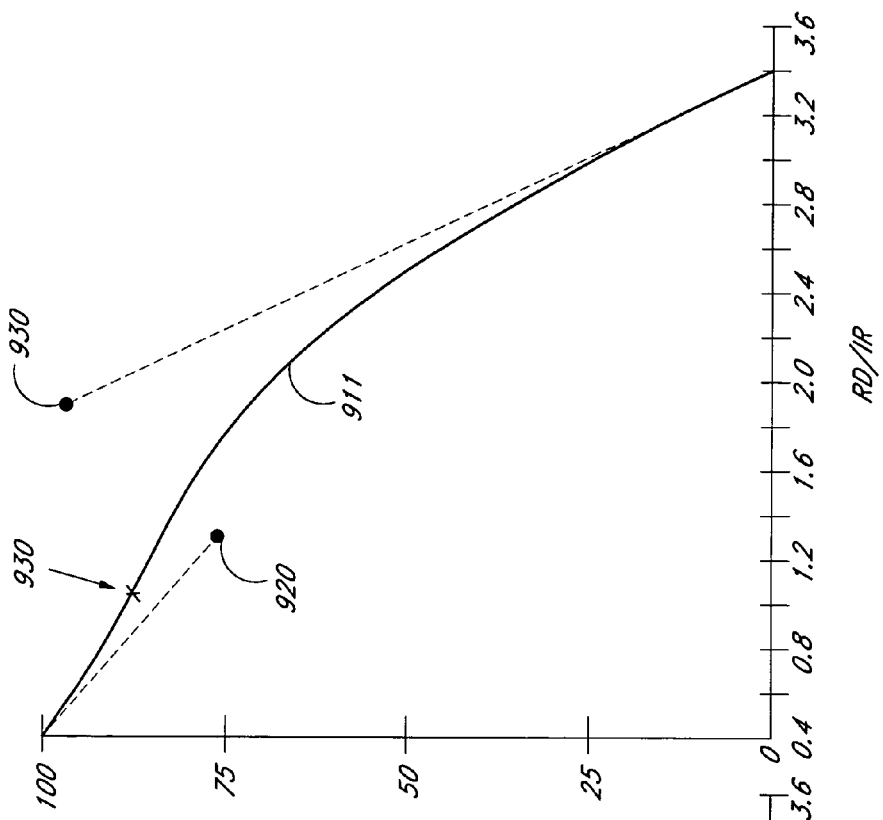
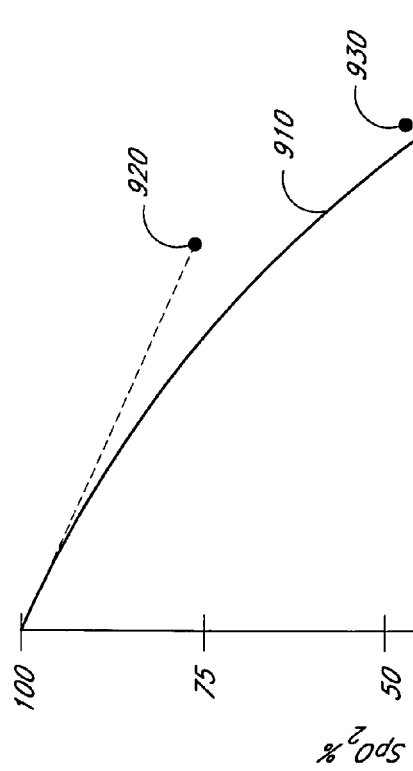
FIG. 9A
FIG. 9B

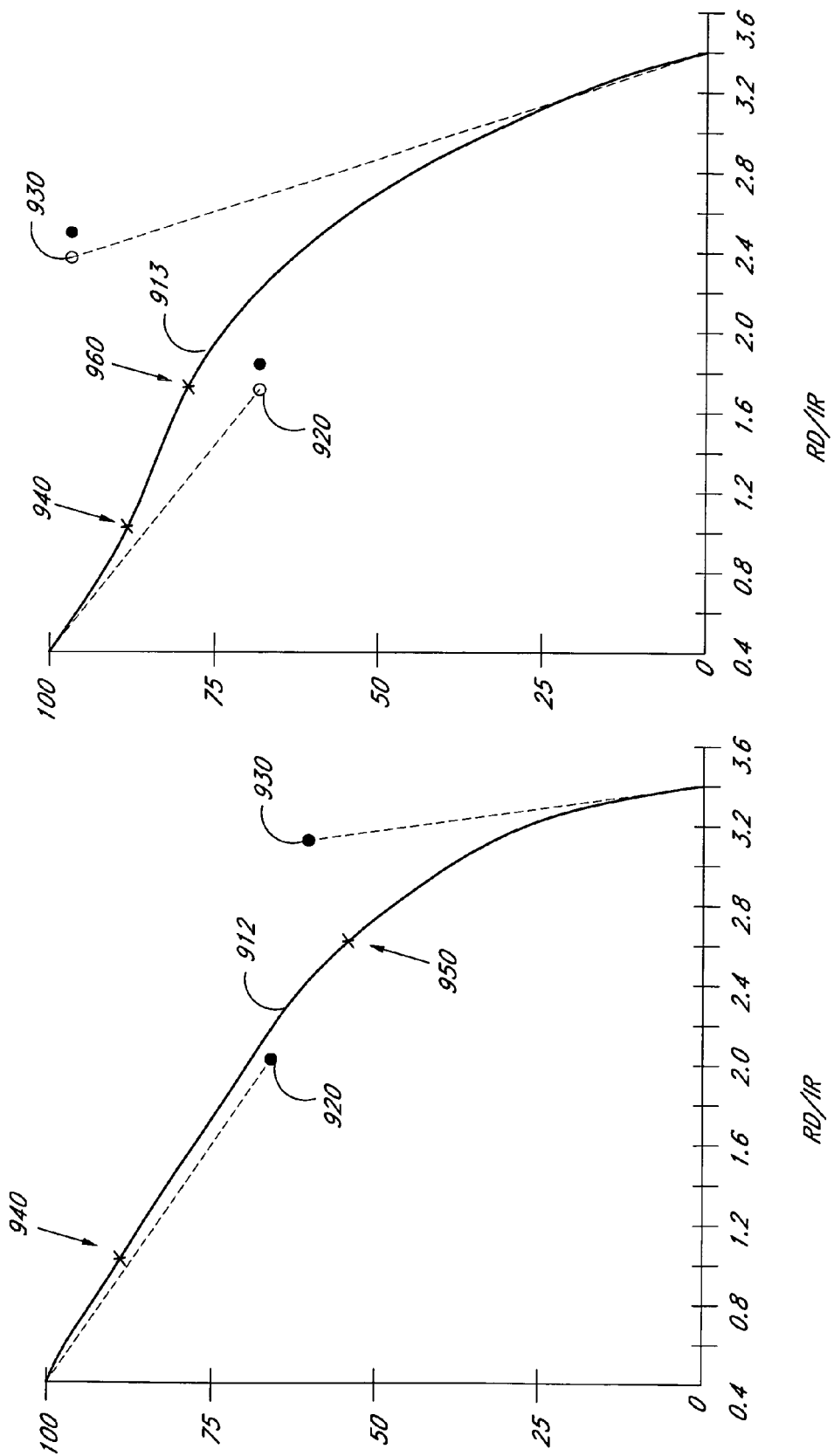

PARAMETER COMPENSATED PHYSIOLOGICAL MONITOR

REFERENCE TO RELATED APPLICATIONS

The present application is a continuation-in-part of U.S. patent application Ser. No. 10/671,179, filed Sep. 25, 2003, entitled "Parameter Compensated Pulse Oximeter," which claims the benefit of U.S. Provisional Application No. 60/413,494, filed Sep. 25, 2002, entitled "Parameter Compensated Pulse Oximeter." The present application also claims the benefit U.S. Provisional Application No. 60/426,638, filed Nov. 16, 2002, entitled "Parameter Compensated Physiological Monitor." The present application incorporates the disclosures of the foregoing applications herein by reference.

BACKGROUND OF THE INVENTION

Pulse oximetry is a noninvasive, easy to use, inexpensive procedure for measuring the oxygen saturation level of arterial blood. Pulse oximeters perform a spectral analysis of the pulsatile component of arterial blood in order to determine the relative concentration of oxygenated hemoglobin, the major oxygen carrying constituent of blood, and reduced hemoglobin. These instruments have gained rapid acceptance in a wide variety of medical applications, including surgical wards, intensive care units, general wards and home care by providing early detection of decreases in the arterial oxygen supply, which reduces the risk of accidental death and injury.

FIG. 1 illustrates a pulse oximetry system 100 having a sensor 110 and a monitor 150. The sensor 110 has emitters 120 and a detector 130. The emitters 120 typically consist of a red light emitting diode (LED) and an infrared LED that project light through blood vessels and capillaries underneath a tissue site, such as a fingernail bed. The detector 130 is typically a photodiode positioned opposite the LEDs so as to detect the emitted light as it emerges from the tissue site. A pulse oximetry sensor is described in U.S. Pat. No. 6,088,607 entitled "Low Noise Optical Probe," which is assigned to Masimo Corporation, Irvine, Calif. and incorporated by reference herein.

Also shown in FIG. 1, the monitor 150 has drivers 152, a sensor front-end 154, a signal processor 155, a display driver 157, a display 158 and a controller 159. The drivers 152 alternately activate the emitters 120 as determined by the controller 159. The front-end 154 conditions and digitizes the resulting current generated by the detector 130, which is proportional to the intensity of the detected light. The signal processor 155 inputs the conditioned detector signal and determines oxygen saturation based upon the differential absorption by arterial blood of the two wavelengths projected by the emitters 120. Specifically, a ratio of detected red and infrared intensities is calculated by the signal processor 155, and an arterial oxygen saturation value is empirically determined based on the ratio obtained, as described with respect to FIGS. 2–3, below. The display driver 157 and associated display 158 indicate a patient's oxygen saturation along with pulse rate.

The Beer-Lambert law provides a simple model that describes a tissue site response to pulse oximetry measurements. The Beer-Lambert law states that the concentration $c_i$ of an absorbent in solution can be determined by the intensity of light transmitted through the solution, knowing the pathlength $d_\lambda$, the intensity of the incident light $I_{0,\lambda}$, and the extinction coefficient $\epsilon_{i,\lambda}$ at a particular wavelength $\lambda$. In generalized form, the Beer-Lambert law is expressed as:

$$I_\lambda = I_{0,\lambda} e^{-d_\lambda \mu_{a,\lambda}} \tag{1}$$

$$\mu_{a,\lambda} = \sum_{i=1}^{n} \epsilon_{i,\lambda} \cdot c_i \tag{2}$$

where $\mu_{a,\lambda}$ is the bulk absorption coefficient and represents the probability of absorption per unit length. The Beer-Lambert law assumes photon scattering in the solution is negligible. The minimum number of discrete wavelengths that are required to solve EQS. 1–2 are the number of significant absorbers that are present in the solution. For pulse oximetry, it is assumed that wavelengths are chosen such that there are only two significant absorbers, which are oxygenated hemoglobin ($HbO_2$) and reduced hemoglobin (Hb).

FIG. 2 illustrates top-level computation functions for the signal processor 155 (FIG. 1), described above. In particular, pulse oximetry measurements are conventionally made at a red wavelength corresponding to 660 nm and an infrared wavelength corresponding to 940 nm. At these wavelengths, reduced hemoglobin absorbs more red light than oxygenated hemoglobin, and, conversely, oxygenated hemoglobin absorbs more infrared light than reduced hemoglobin.

In addition to the differential absorption of hemoglobin derivatives, pulse oximetry relies on the pulsatile nature of arterial blood to differentiate hemoglobin absorption from absorption of other constituents in the surrounding tissues. Light absorption between systole and diastole varies due to the blood volume change from the inflow and outflow of arterial blood at a peripheral tissue site. This tissue site also comprises skin, muscle, bone, venous blood, fat, pigment, etc., each of which absorbs light. It is assumed that the background absorption due to these surrounding tissues is invariant and can be ignored. That is, the sensor signal generated by the pulse-added arterial blood is isolated from the signal generated by other layers including tissue, venous blood and baseline arterial blood.

As shown in FIG. 2, to isolate the pulsatile arterial blood, the signal processor 155 (FIG. 1) computes ratios 215, 265 of the AC portions 212, 262 of the detected red (RD) 201 and infrared (IR) 206 signals with respect to the DC portions 214, 264 of the detected signals 201, 206. Computations of these AC/DC ratios 215, 265 provide relative absorption measures that compensate for variations in both incident light intensity and background absorption and, hence, are responsive only to the hemoglobin in the arterial blood. Further, a ratio of the normalized absorption at the red wavelength over the normalized absorption at the infrared wavelength is computed:

$$RD/IR = (Red_{AC}/Red_{DC})/(IR_{AC}/IR_{DC}) \tag{3}$$

The desired oxygen saturation ($SpO_2$) 282 is then computed empirically from this "red-over-infrared, ratio-of-ratios" (RD/IR) 272. That is, the RD/IR output 272 is input to a look-up table 280 containing empirical data 290 relating RD/IR to $SpO_2$, as described with respect to FIG. 3, below.

FIG. 3 shows a graph 300 depicting the relationship between RD/IR and $SpO_2$. This relationship can be approximated from Beer-Lambert's Law, described above. However, it is most accurately determined by statistical regression of experimental measurements obtained from human volunteers and calibrated measurements of oxygen saturation. The result can be depicted as a curve 310, with measured values of RD/IR shown on a x-axis 302 and corresponding saturation values shown on an y-axis 301. In a pulse oximeter device, this empirical relationship can be stored in a read-only memory (ROM) for use as a look-up table 280 (FIG. 2) so that $SpO_2$ can be directly read-out from an input RD/IR measurement. For example, an RD/IR value of 1.0 corresponding to a point 312 on the calibration curve 310 indicates a resulting $SpO_2$ value of approximately 85%.

SUMMARY OF THE INVENTION

Conventional pulse oximetry measurements, for example, depend on a predictable, empirical correlation between RD/IR and $SpO_2$. The relationship between oxygen saturation and tissue spectral characteristics, such as RD absorbance as compared with IR absorbance, however, vary with other parameters such as site temperature, pH and total hematocrit (Hct), to name just a few, that are not accounted for in the conventional photon absorbance model. A parameter compensated physiological monitor advantageously utilizes one or more parameters that are not considered in conventional physiological monitoring in order to derive a more accurate physiological measurement. Parameters may be input from various sources, such as multiple parameter sensors, additional sensors, external instrumentation and manual input devices. A compensated physiological measurement accounts for these parameters by various mechanisms including modification of calibration data, correction of uncompensated physiological measurements, multidimensional calibration data, sensor wavelength modification in conjunction with wavelength-dependent calibration data, and modification of physiological measurement algorithms.

One aspect of a parameter compensated physiological monitor has a primary input from which a spectral characteristic of a tissue site can be derived. The monitor also has a secondary input from which at least one parameter can be determined. A compensation relationship of the spectral characteristic, the parameter and a compensated physiological measurement is determined. A processor is configured to output the compensated physiological measurement in response to the primary input and the secondary input utilizing the compensation relationship.

A parameter compensated physiological monitoring method includes the steps of inputting a sensor signal responsive to a spectral characteristic of a tissue site and deriving a physiological measurement from the characteristic. Other steps include obtaining a parameter, wherein the physiological measurement has a dependency on the parameter and determining a relationship between the spectral characteristic and the parameter that accounts for the dependency. A further step is compensating the physiological measurement for the parameter utilizing the relationship.

Another aspect of a parameter compensated physiological monitor has a primary input for determining a spectral characteristic associated with a tissue site. The monitor also has a secondary input means for determining a parameter that is relevant to measuring oxygen saturation at the tissue site and a compensation relationship means for relating the spectral characteristic, the parameter and an oxygen saturation measurement.

BRIEF DESCRIPTION OF THE DRAWINGS

FIGS. 9A–D are graphs of one embodiment of calibration data modification utilizing Bezier curves.

DETAILED DESCRIPTION OF THE PREFERRED EMBODIMENT

Overview

Figure 4:
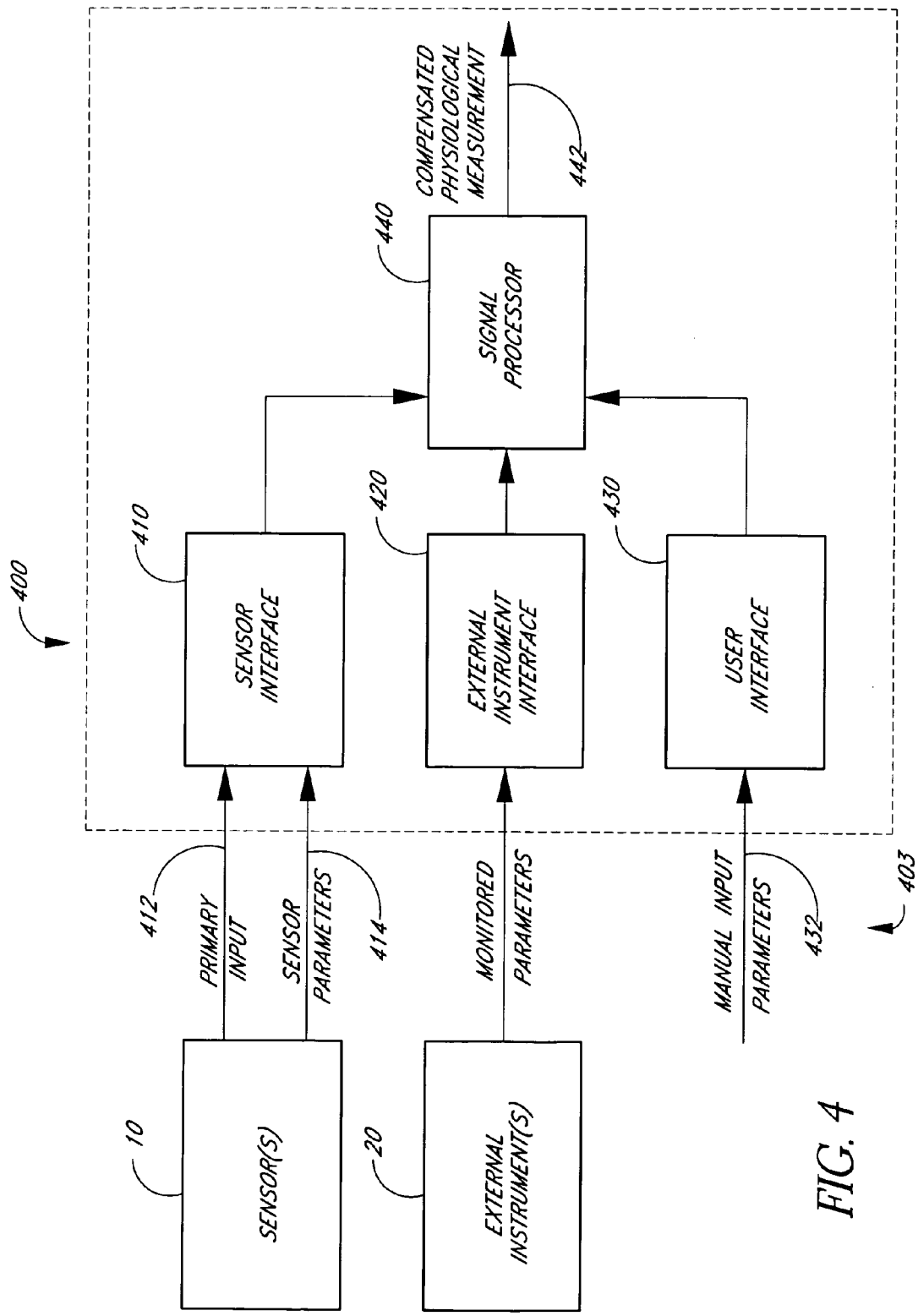
FIG. 4 is a top-level block diagram of a parameter compensated physiological monitor having sensor, external instrument and manual parameter inputs.
Figure 5:
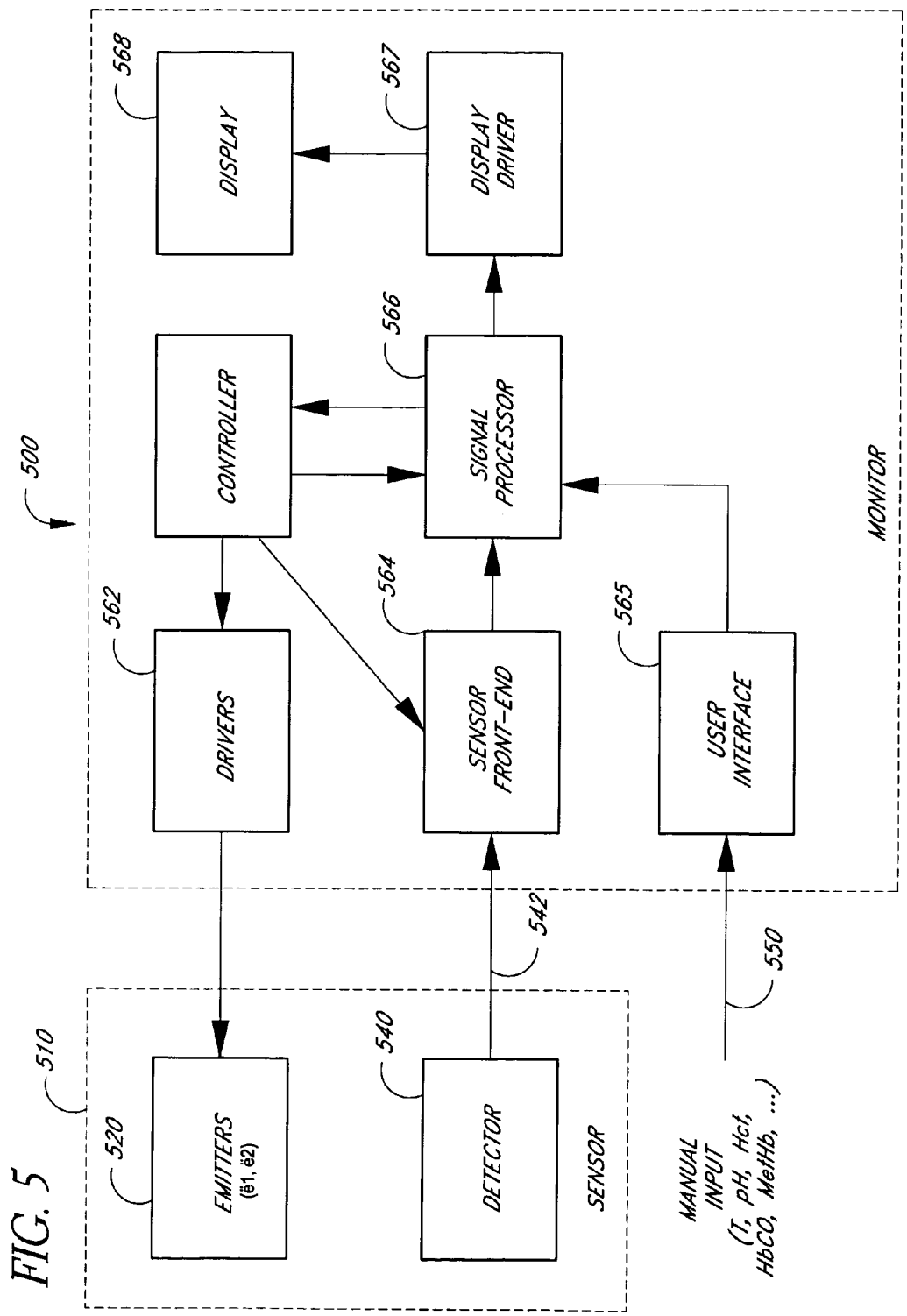
FIG. 5 is a block diagram of a parameter compensated pulse oximeter having a manual parameter input.
Figure 6:
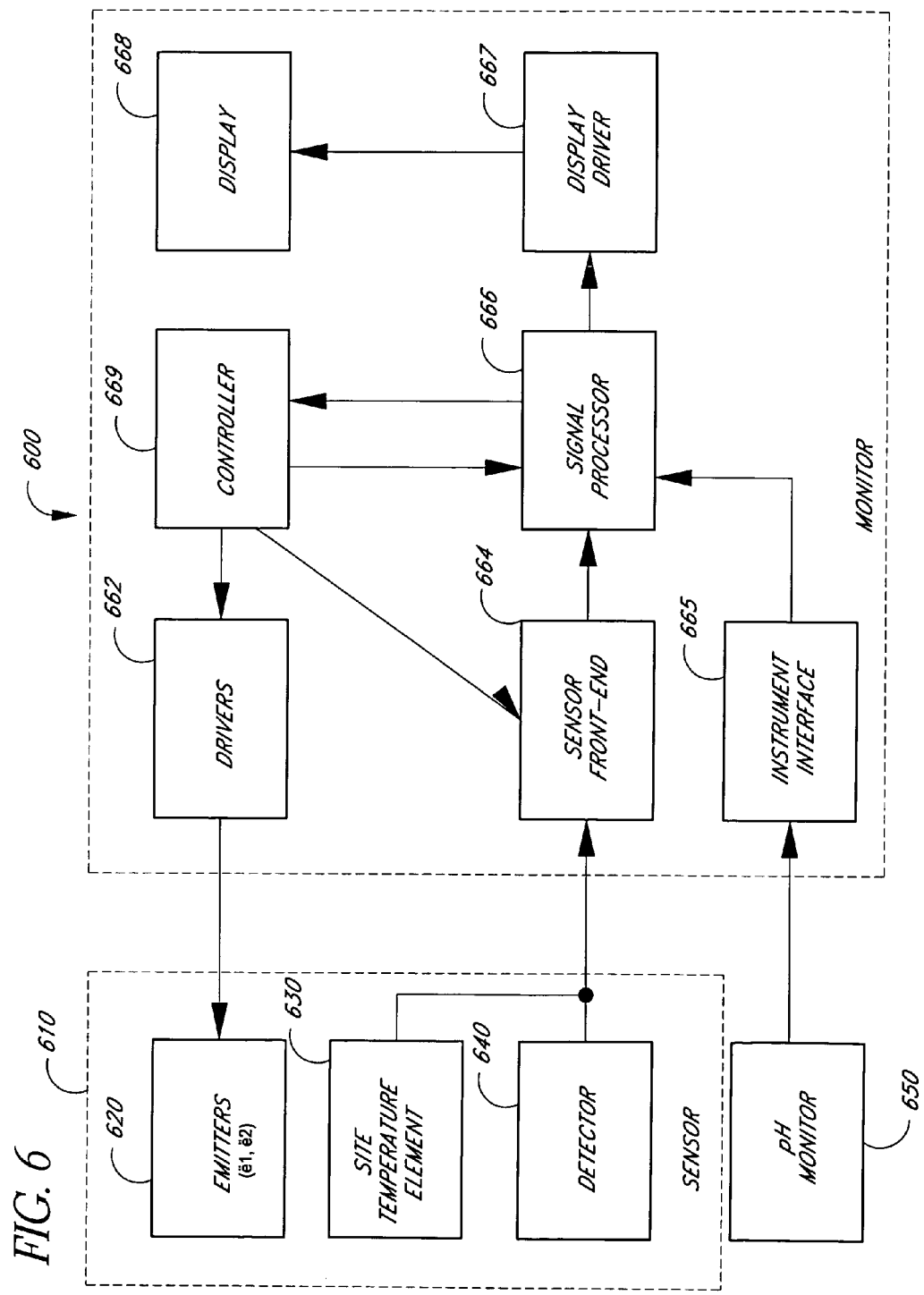
FIG. 6 is a block diagram of a parameter compensated pulse oximeter having a multi-wavelength sensor along with sensor site temperature and external instrument pH parameter inputs.

Parameter compensated physiological monitoring is described below with respect to monitor interface architectures (FIGS. 4–6) and monitor signal processing functions (FIGS. 7–14). FIG. 4 illustrates a general interface architecture including a primary sensor input and parameter inputs from sensors, external instruments and manual entry. FIGS. 5–6 illustrate particular pulse oximetry embodiments of FIG. 4. FIG. 5 illustrates a two-wavelength sensor input along with manual parameter inputs. FIG. 6 illustrates a multiple wavelength sensor allowing derived parameters, a sensor temperature element input for a site temperature parameter, and an external instrument input for a pH parameter.

Figure 7:
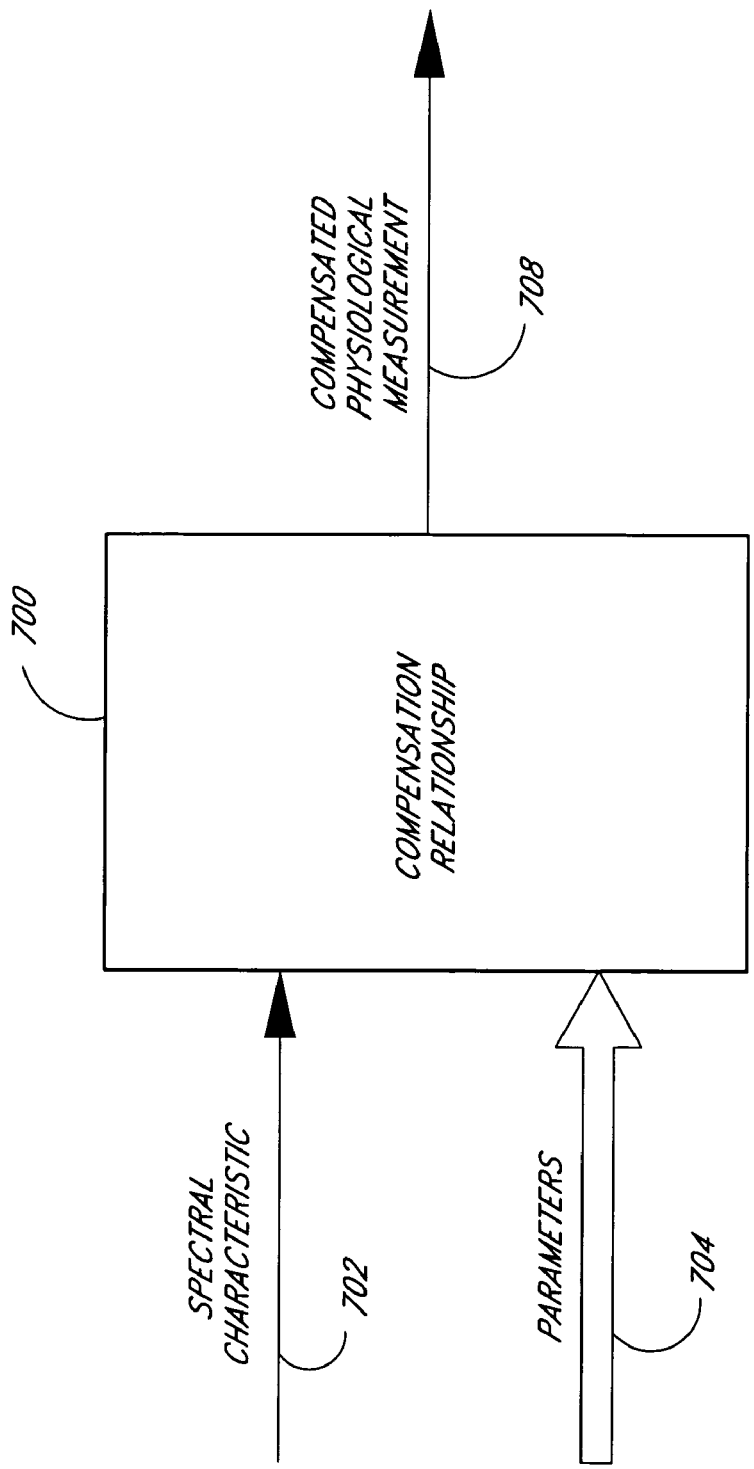
FIG. 7 is a top-level functional block diagram of a compensation relationship having spectral characteristic and parameter inputs and a compensated physiological measurement output.
Figure 10A:
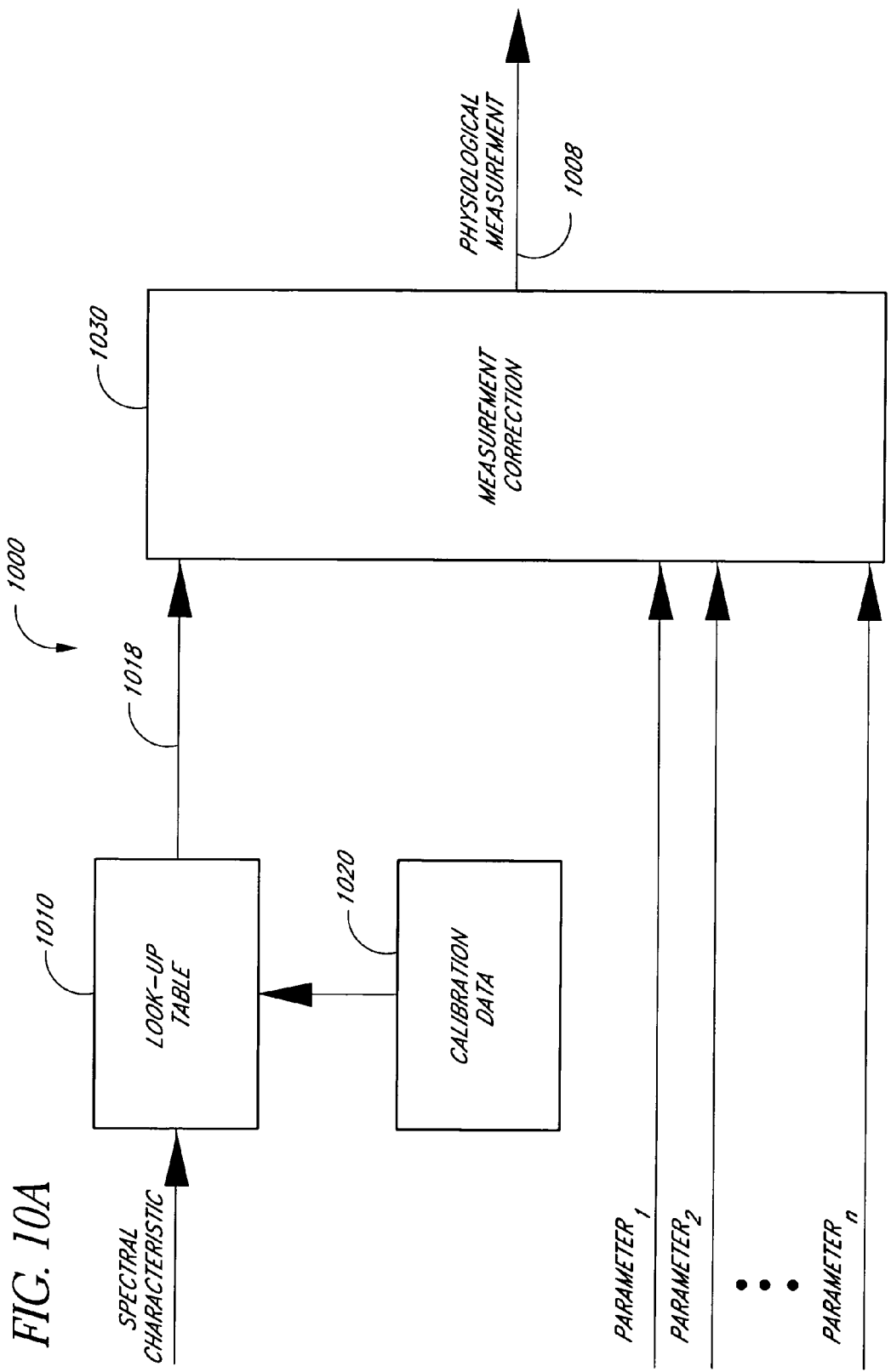
FIG. 10A is a functional block diagram of parameter compensated signal processing incorporating physiological measurement correction.
Figure 10B:
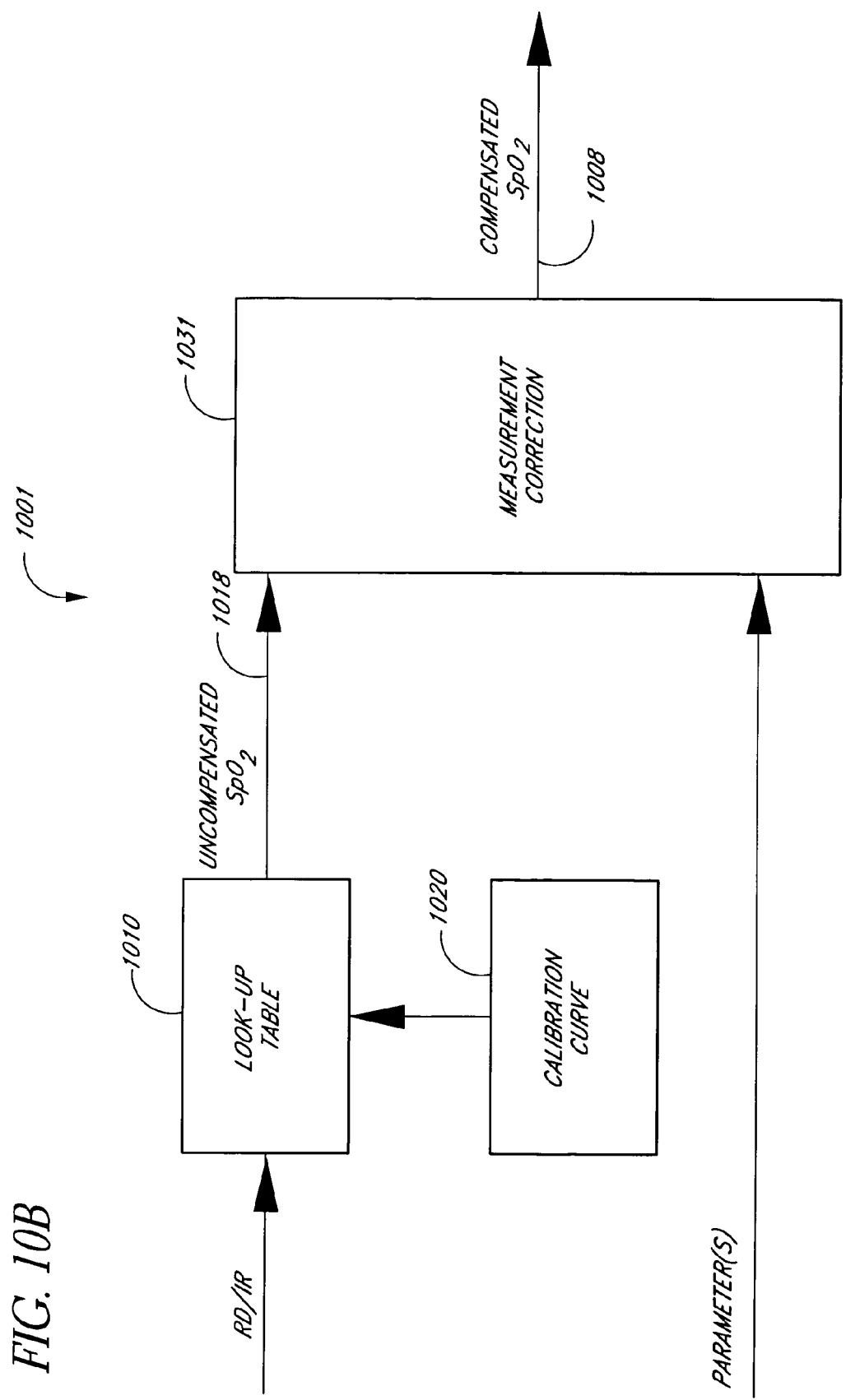
FIG. 10B is a functional block diagram of compensated pulse oximetry incorporating a hemoglobin constituent correction for a $SpO_2$ measurement.
Figure 11:
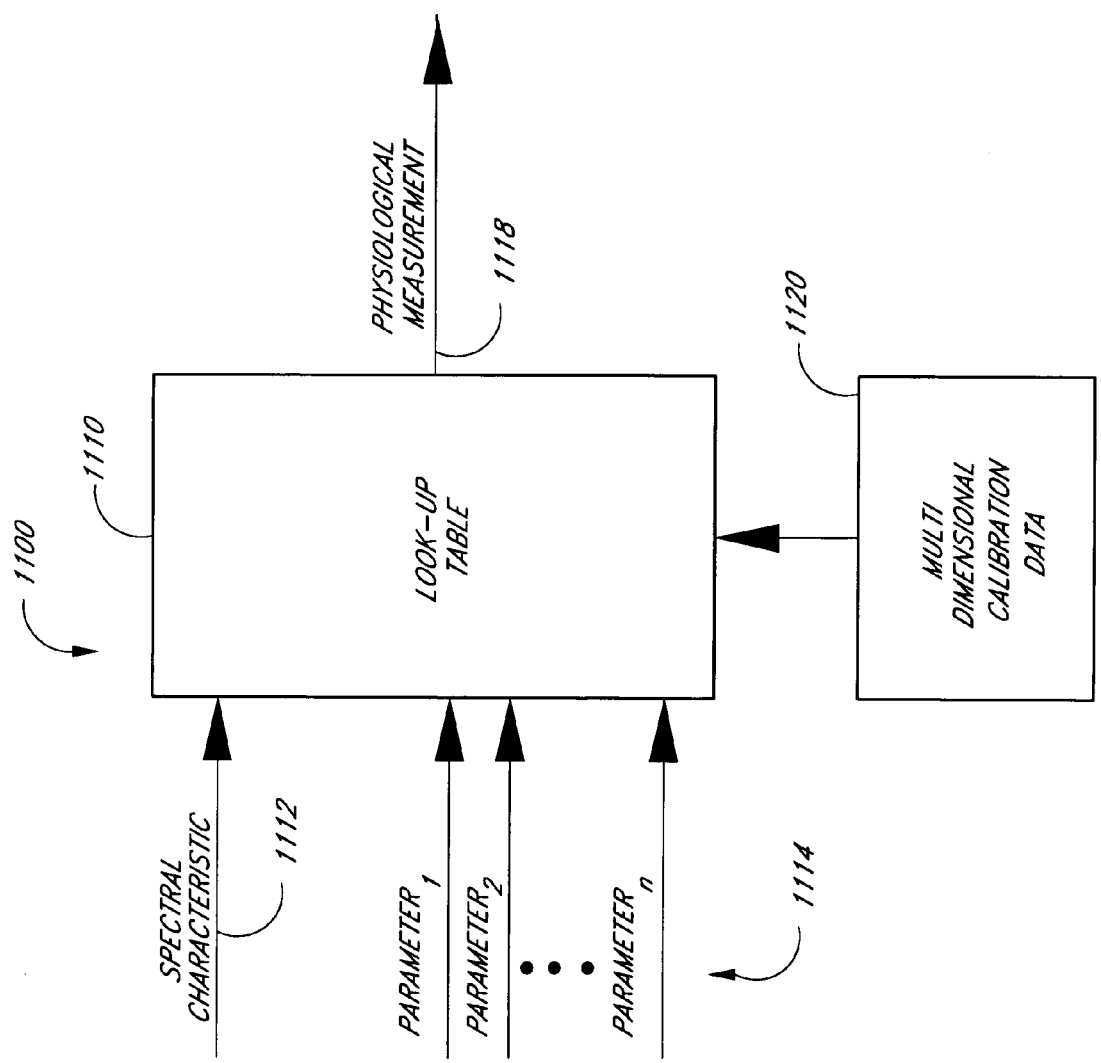
FIG. 11 is a functional block diagram of parameter compensated signal processing incorporating multidimensional calibration data.
Figure 12:
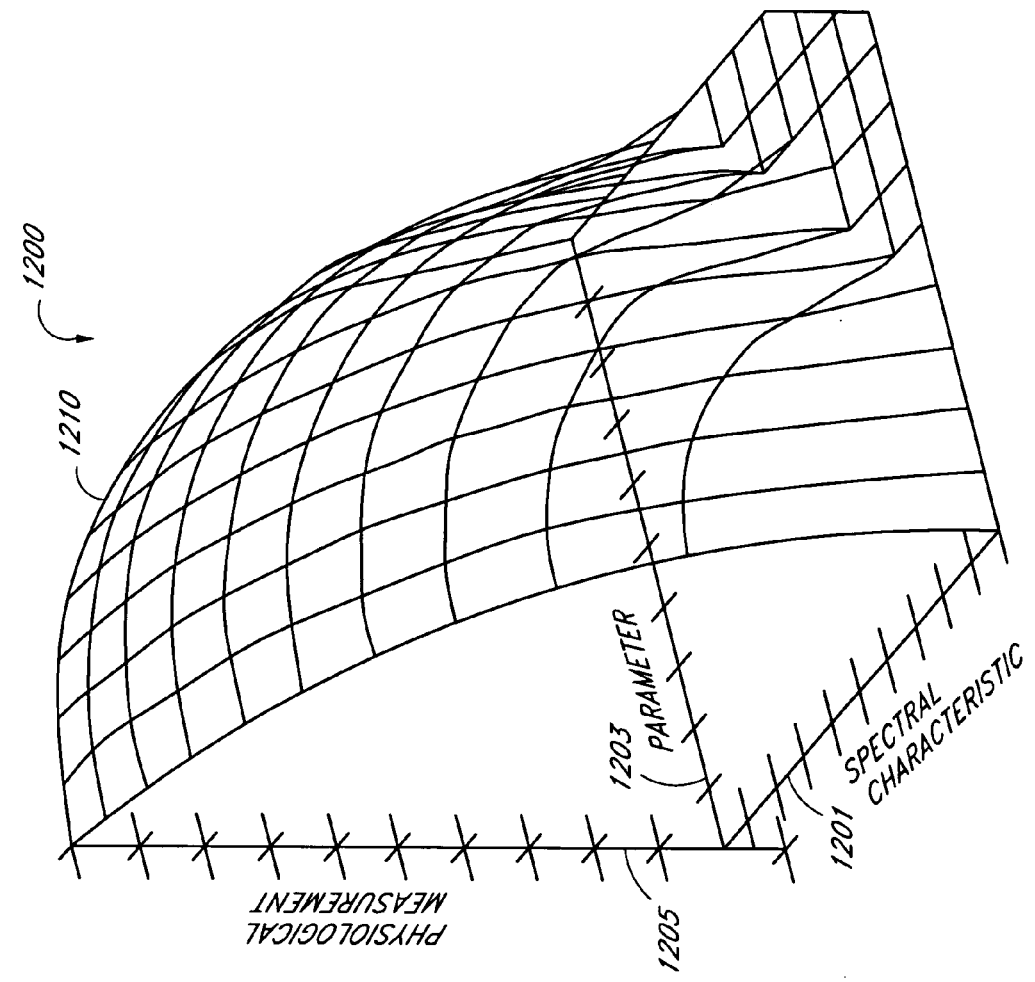
FIG. 12 is a graph of a multidimensional calibration surface for a compensated physiological measurement.
Figure 13A:
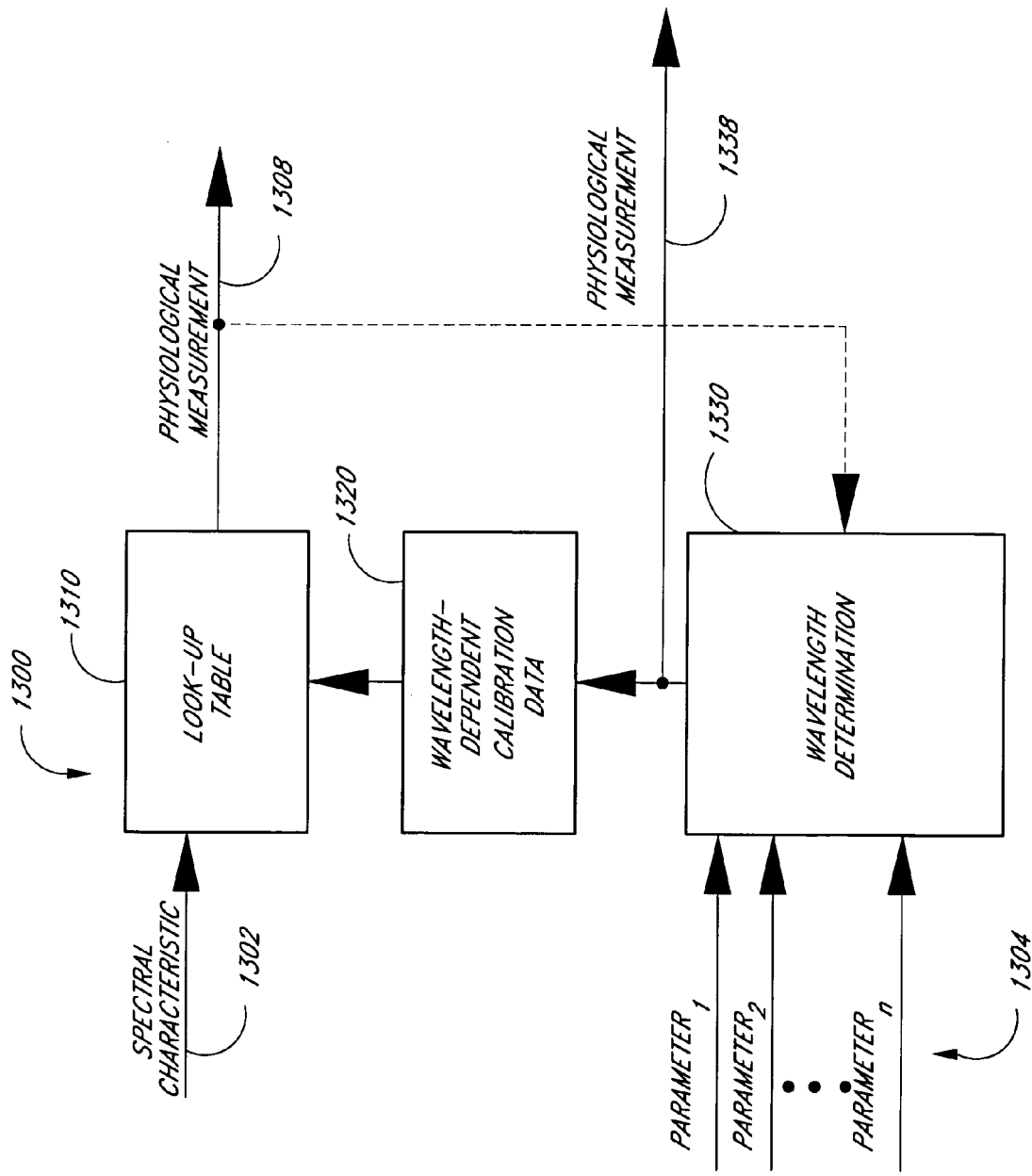
FIG. 13A is a functional block diagram of parameter compensated signal processing incorporating sensor wavelength modification and wavelength-dependent calibration data.
Figure 13B:
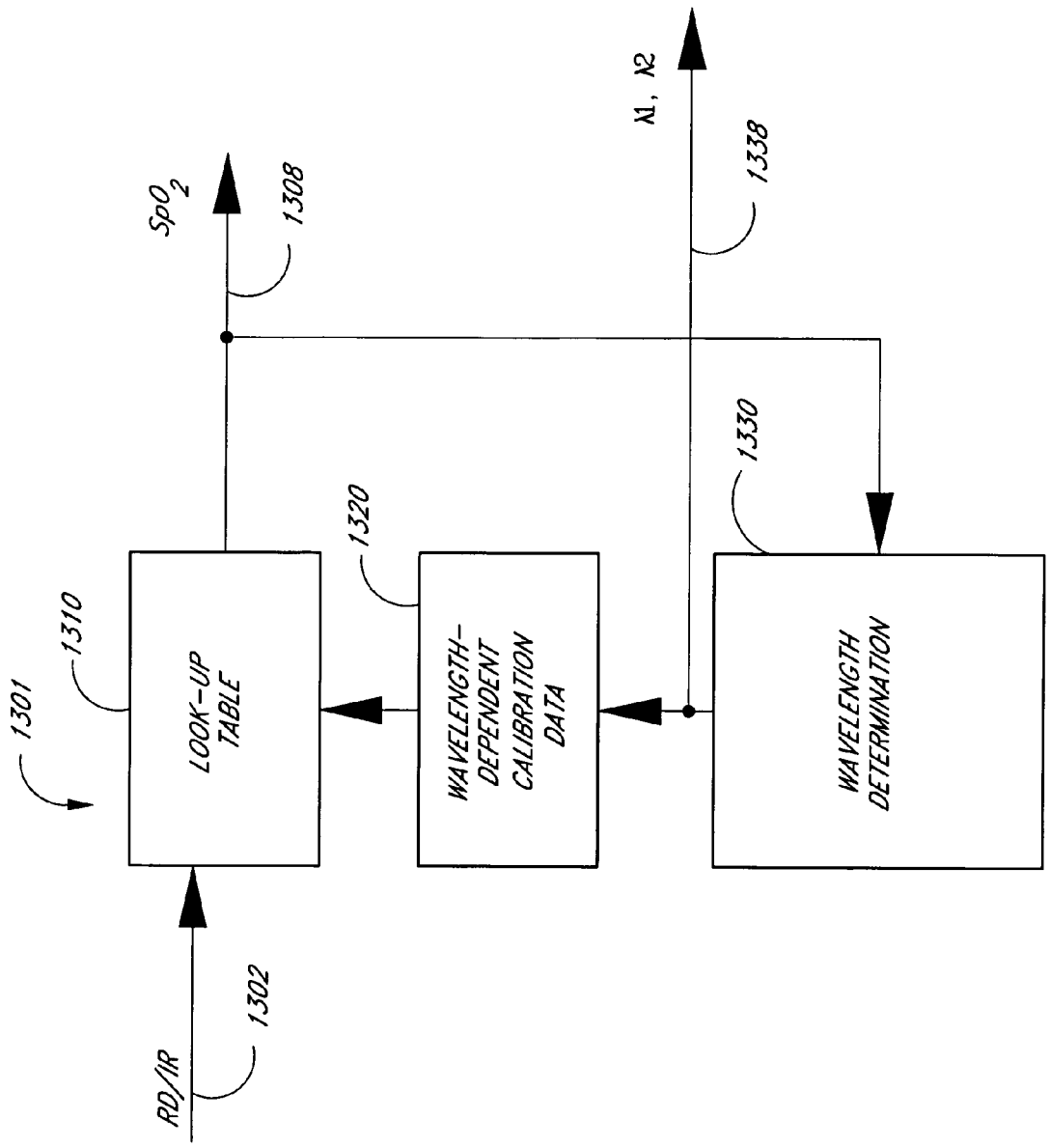
FIG. 13B is a functional block diagram of compensated pulse oximetry incorporating a null parameter and $SpO_2$ feedback.
Figure 14:
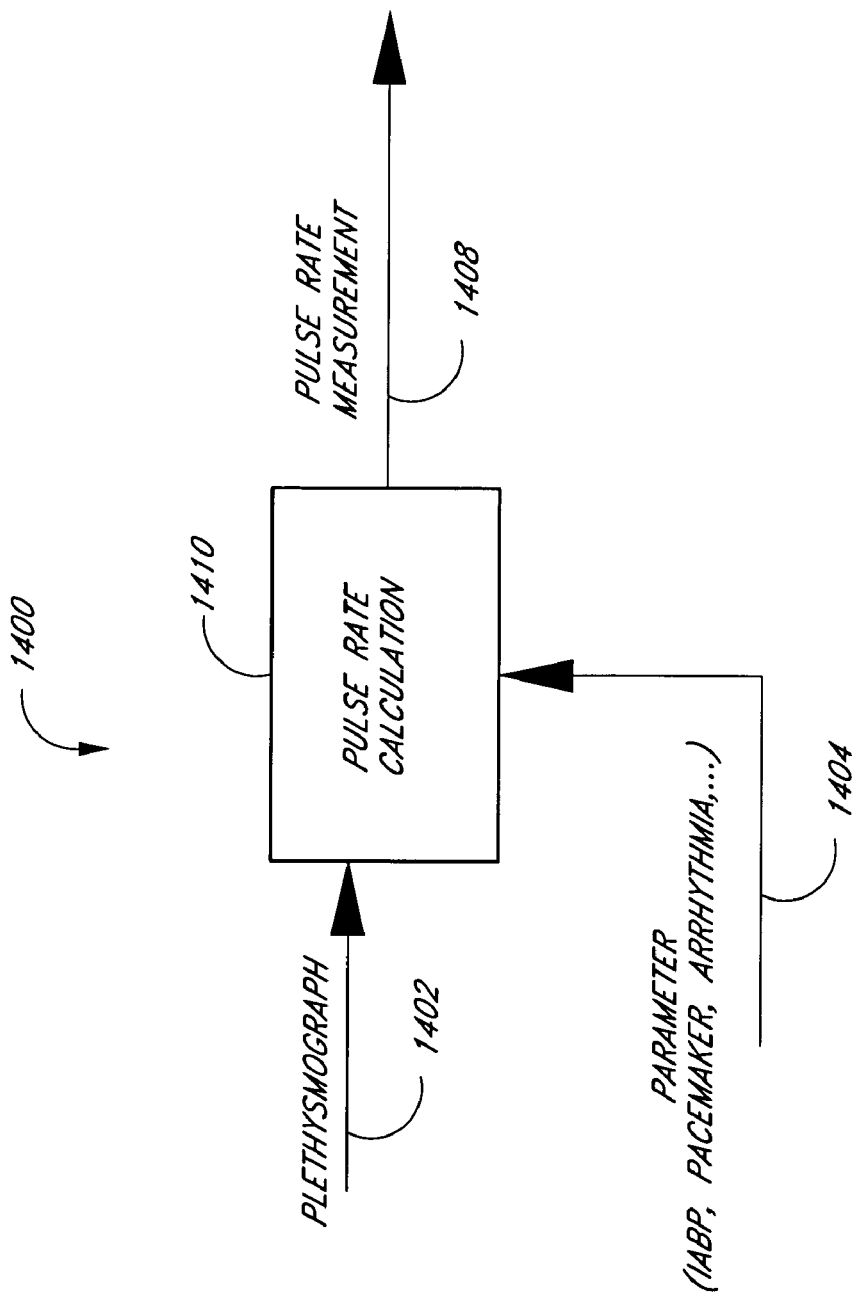
FIG. 14 is a functional block diagram of compensated pulse rate measurements.

FIG. 7 illustrates a general parameter compensation signal processing function. FIGS. 8–9 illustrate a compensated physiological measurement computed from a spectral characteristic utilizing parameter modified calibration data. FIGS. 10A–B illustrate a compensated physiological measurement computed from parameter dependent correction of an uncompensated physiological measurement. FIGS. 11–12 illustrate a compensated physiological measurement computed from a spectral characteristic and input parameters utilizing multidimensional calibration data. FIGS. 13A–B illustrate a compensated physiological measurement resulting from parameter dependent sensor wavelength and calibration data modification. FIG. 14 illustrates a compensated physiological measurement computed from a parameter modified algorithm.

The interface architectures according to FIGS. 4–6 may each support signal processing functions according to FIGS. 7–14. As just one of many examples and embodiments, a pulse oximeter has a manual input compensation parameter, such as described with respect to FIG. 5. The manual input may be, say, a blood gas derived parameter, such as carboxyhemoglobin (HbCO) or methemoglobin (MetHb) to name just a few. This parameter is utilized to select, modify, derive or otherwise determine a calibration curve or other form of calibration data so as to compute a more accurate measure of $SpO_2$.

Parameter Compensation Architecture

FIG. 4 illustrates a parameter compensated physiological monitor 400 having a sensor interface 410, an external instrument interface 420 and a user interface 430. The sensor interface 410 connects to one or more tissue site sensors 10, which may be optical or non-optical devices configured to provide invasive or noninvasive measurements of tissue site properties. The sensor interface 410 has a primary input 412 and one or more sensor parameter inputs 414. The primary input 412 is adapted to provide tissue site spectral characteristics via sensor optical elements. A sensor parameter input 414 is adapted to provide other tissue site characteristics via optical or nonoptical elements.

Figure 1:
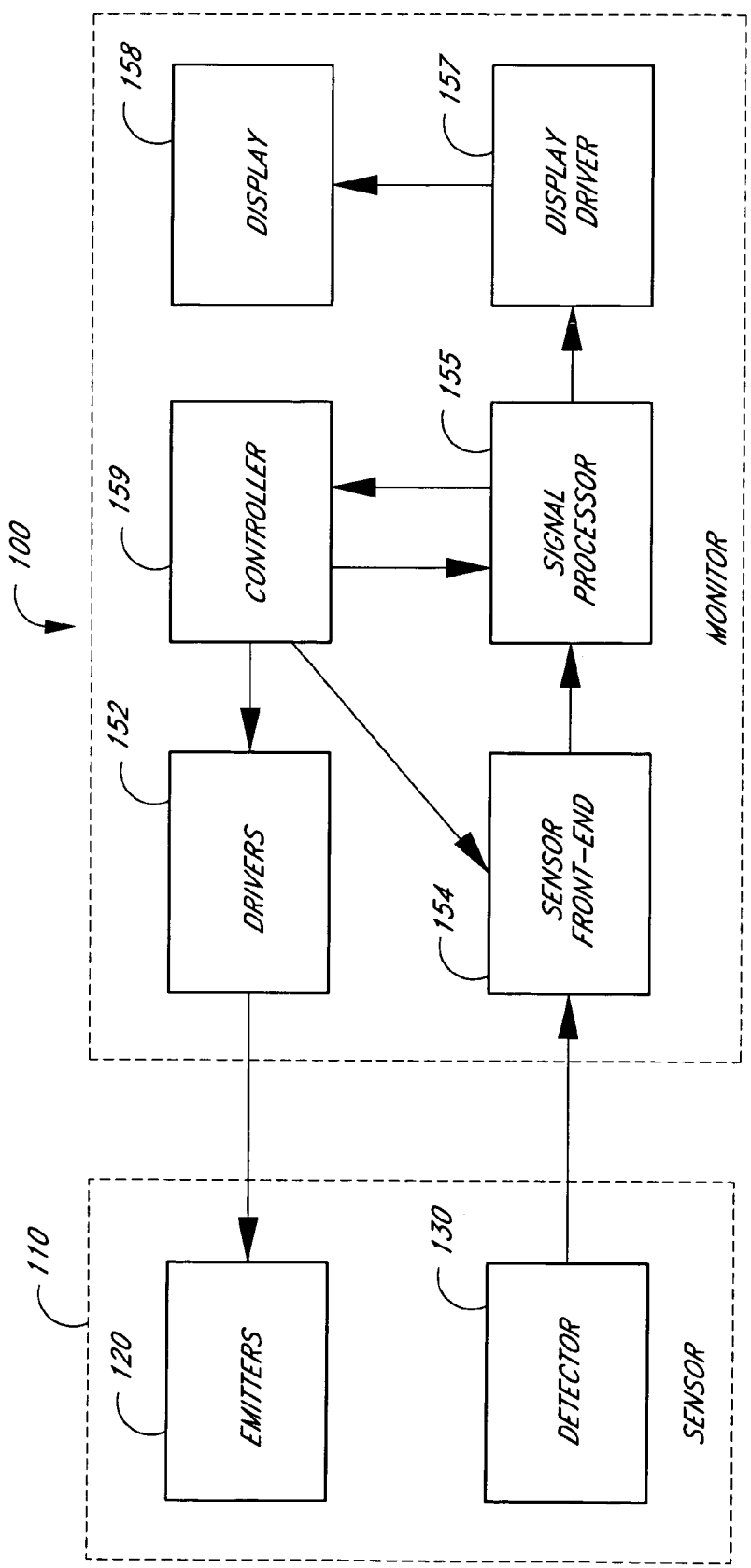
FIG. 1 is a block diagram of a prior art pulse oximeter.
Figure 2:
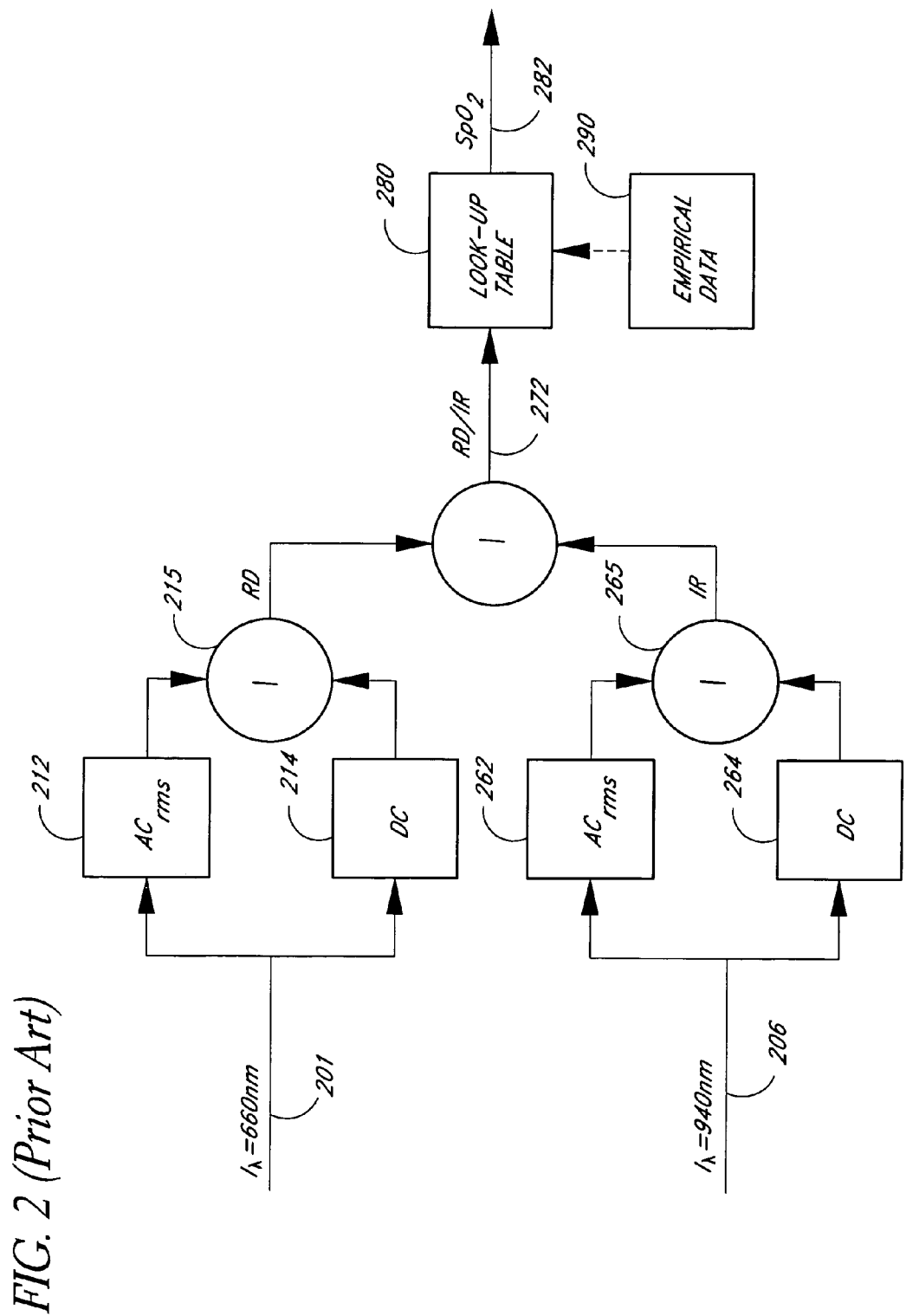
FIG. 2 is a top-level functional diagram of conventional pulse oximetry signal processing.
Figure 3:
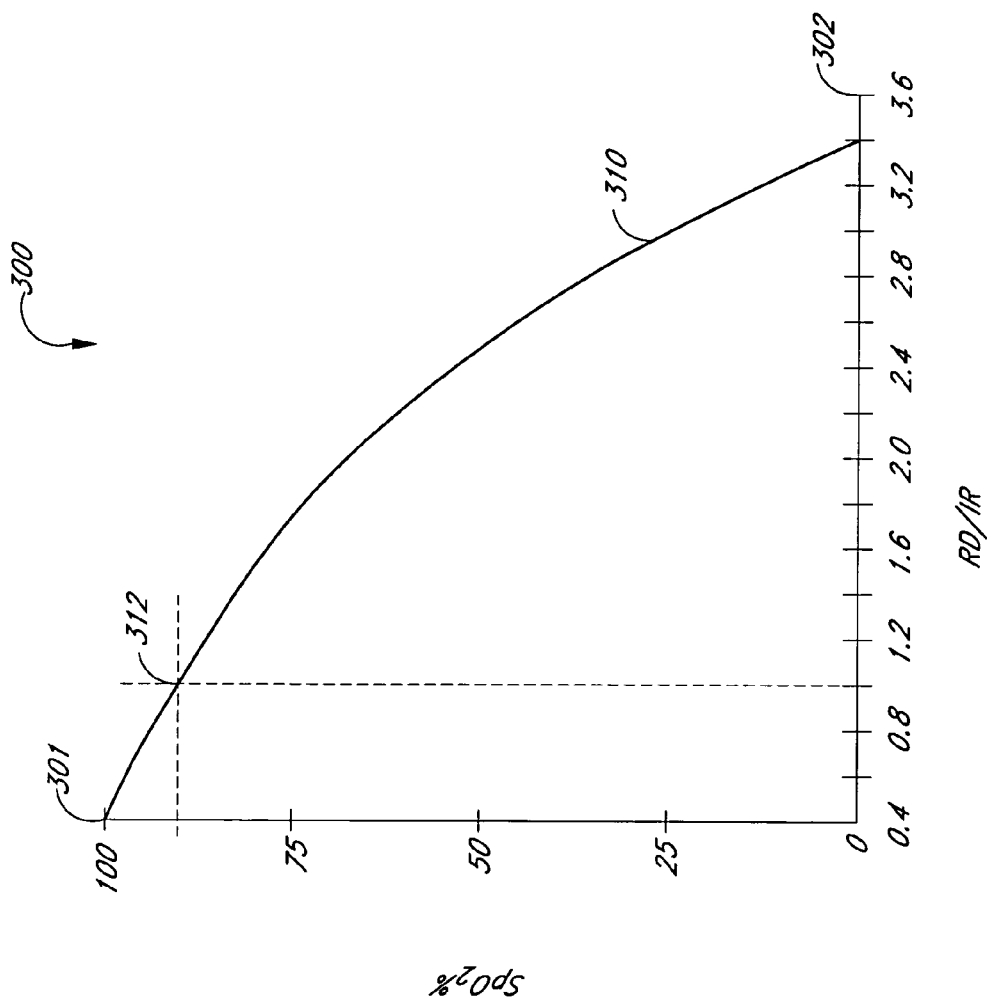
FIG. 3 is an exemplar graph of a conventional calibration curve.

In one embodiment, the primary input 412 is a detector response to at least two emitter wavelengths after transmission through or reflection from a tissue site, from which the physiological monitor 400 may derive at least a conventional physiological measurement, such as an oxygen saturation value, as described with respect to FIGS. 1–3 above. An example of this embodiment is described with respect to FIG. 5, below. In another embodiment, the sensor 10 utilizes more than two wavelengths so that the physiological monitor 400 may derive, for example, the concentrations of other blood constituents in addition to oxygen saturation, such as total hematocrit (Hct). The same sensor or a different sensor may also provide other tissue site measurements, such as temperature, on the sensor parameter input 414. An example of this embodiment is described with respect to FIG. 6, below.

Also shown in FIG. 4, an external instrument interface 420 connects to one or more external instruments 20, which may monitor physiological or nonphysiological properties, invasively or noninvasively, from the sensor tissue site or from other portions of a patient or a patient's immediate environment. In one embodiment, the external instrument 20 is a pH monitor, as described with respect to FIG. 6, below.

Further shown in FIG. 4, a user interface 430 accepts one or more manual input parameters 432. As an example, the user interface 430 may be a keyboard input operating in conjunction with a user display, which may range from a small character display to a CRT providing a computer-generated graphical user interface (GUI). The manual inputs may be any information related to, for instance, a patient, a patient's immediate environment, or a patient's medical history. In one embodiment, a manual input 432 may indicate the presence of an implant device, such as a pacemaker or an intra aortic balloon pump (IABP). In another embodiment, a manual input of blood gas measurements, such as are obtainable from a CO-oximeter, is provided.

Additionally shown in FIG. 4, the sensor interface 410, external instrument interface 420 and user interface 430 each provide inputs to the signal processor 440. The signal processor utilizes the primary input 412 and one or more parameter inputs 403 to generate a compensated physiological measurement 442. In one embodiment, the compensated physiological measurement 442 is an $SpO_2$ value that is derived from both the primary input 412 and the parameter inputs 403.

FIG. 5 illustrates one embodiment of a parameter compensated physiological monitor 400 (FIG. 4). A parameter compensated pulse oximeter 500 has sensor 510 and manual inputs. In particular, drivers 562 activate emitters 520 that project two wavelengths into a tissue site, and a detector 540 responsive to the emitters 520 provides a primary input 542 to a sensor front-end 564, as described above. A user interface 565 accepts manual inputs 550 such as temperature (T), pH, Hct, HbCO and MetHb, etc. The sensor front-end 564 and user interface 565 output to the signal processor 566 a detector signal along with the manually input parameters. The signal processor 566 computes a compensated $SpO_2$ measurement from the detector signal and these parameters, as described with respect to FIGS. 7–13, below. The compensated $SpO_2$ measurement is then displayed 567, 568 in a manner similar to that described above with respect to FIG. 1.

FIG. 6 illustrates another embodiment of a parameter compensated physiological monitor 400 (FIG. 4). A parameter compensated multiple wavelength monitor 600 has inputs from a sensor 610 and an external pH monitor 650. The sensor 610 has multiple wavelength emitters 620 and a site temperature element 630. Multiple wavelengths may be achieved, for example, by utilizing multiple LEDs each manufactured for a specific wavelength according to the number of wavelengths desired. Alternatively, one or more LEDs having drive current dependent wavelengths may be utilized, where the drive current is controlled to shift between multiple wavelengths. The site temperature element 630 provides a site temperature parameter input to the sensor front-end 664. In one embodiment, the site temperature element 630 is a thermistor located on the sensor 610 proximate the emitters 620 or proximate the detector 640. The detector 640 provides a multiple wavelength signal output that is combined with a site temperature output to a sensor front-end 664. An instrument interface 665 is adapted to input pH readings from the pH monitor 650. The sensor drivers 662 provide multiplexed activation of the multiple emitters 620 as determined by the controller 669. The signal processor 666 accepts outputs from the sensor front-end 664 and the instrument interface 665. In addition, the signal processor 666 computes an $SpO_2$ measurement from the detector signal along with a sensor parameter, such as Hct for example, utilizing the multiple wavelength signal from the detector 640. Further, the signal processor 666 derives a compensated $SpO_2$ measurement from the site temperature, pH, and Hct parameters, as described with respect to FIGS. 7–13, below. The compensated $SpO_2$ measurement is then displayed 667, 668 in a manner similar to that described above.

As shown in FIG. 6, a pulse oximetry sensor 610 may be improved for use in conjunction with a parameter compensated pulse oximeter by increasing the number of wavelengths projected by the emitters 620, which allows the resolution of more than two blood constituents, as described above. Further, the sensor 610 may be improved by adding the capability to measure various parameters, such as site temperature. Alternatively, as shown in FIG. 5, pulse oximeter performance can be improved at reduced costs by utilizing simple sensors in conjunction with other instrumentation and/or manual inputs to provide additional input parameters.

The sensor 610 may also have an information element (not shown) that describes information regarding the sensor. In one embodiment, the information element provides the monitor 660 with information regarding available wavelengths for the emitters 620 and/or information regarding the temperature element 630, such as the resistance-temperature characteristics of a thermistor. An information element is described in U.S. Pat. No. 6,011,986 entitled "Manual And Automatic Probe Calibration," assigned to Masimo Corporation, Irvine, Calif. and incorporated by referenced herein.

Parameter Compensation Signal Processing

FIG. 7 illustrates a compensation relationship function 700 that the signal processor 440 (FIG. 4) performs. The compensation relationship 700 has a spectral characteristic input or inputs 702 and parameter inputs 704 and generates a compensated physiological measurement output 708. The spectral characteristic 702 is derived from the primary input 412 (FIG. 4), the parameters 704 are received from the interfaces 410–430 (FIG. 4), and the physiological measurement 708 is provided at the signal processor output 442 (FIG. 4), as described above. FIGS. 8–14, below, illustrate various embodiments of the compensation relationship 700. FIGS. 8–9 illustrate a compensation relationship incorporating parameter modification of baseline calibration data. FIGS. 10A–B illustrate parameter correction of an uncompensated physiological measurement. FIGS. 11–12 illustrate parameter incorporation into multidimensional calibration data. FIGS. 13A–B illustrate parameter modification of sensor wavelength and selection of wavelength-dependent calibration data. FIG. 14 illustrates parameter modification of physiological measurement algorithms.

Figure 8A:
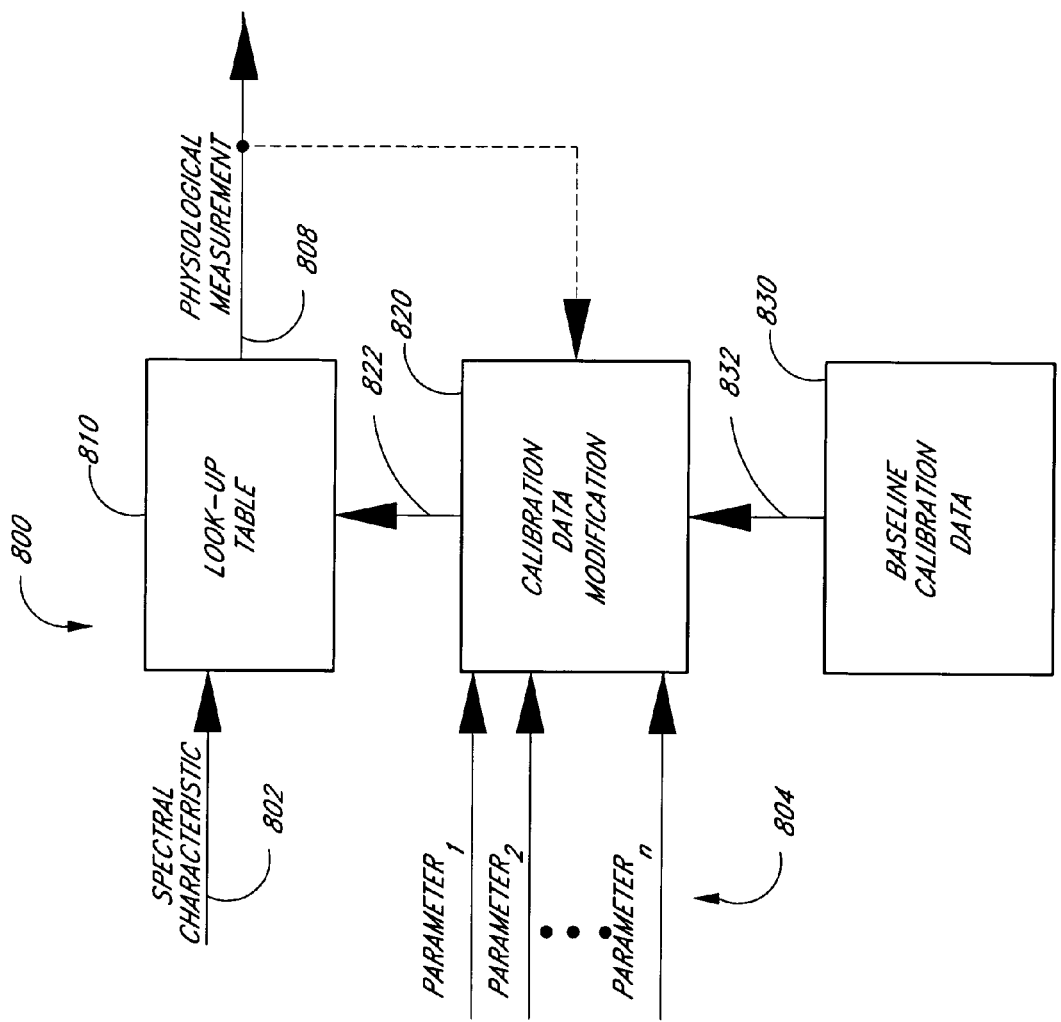
FIG. 8A is a functional block diagram of parameter compensated signal processing incorporating calibration data modification.

FIG. 8A illustrates a compensation relationship 800 having a look-up table 810, baseline calibration data 830 and a calibration data modification function 820. The compensation relationship 800 has a spectral characteristic input 802, parameter inputs 804 and a physiological measurement output 808, as described above. The calibration data modification 820 advantageously responds to the parameters 804 to select, modify, derive or otherwise determine from the baseline calibration data 830 a calibration data input 822 to the look-up table 810. The look-up table 810 uses the calibration data 822 to determine the physiological measurement 808 corresponding to the spectral characteristic 802. The calibration data 822 may also be responsive to feedback of the physiological measurement 808. The baseline calibration data 830 may be determined by statistical regression of experimental measurements obtained from human volunteers and calibrated measurements of the physiological measurement and associated parameters. Also, all or part of the look-up table 810, calibration data modification 820 and baseline calibration data 830 may be replaced by or combined with a mathematical formula or algorithm, theoretically or experimentally derived, that is used to compute calibration data or used to directly compute the physiological measurement from the spectral characteristic and parameter inputs.

Figure 8B:
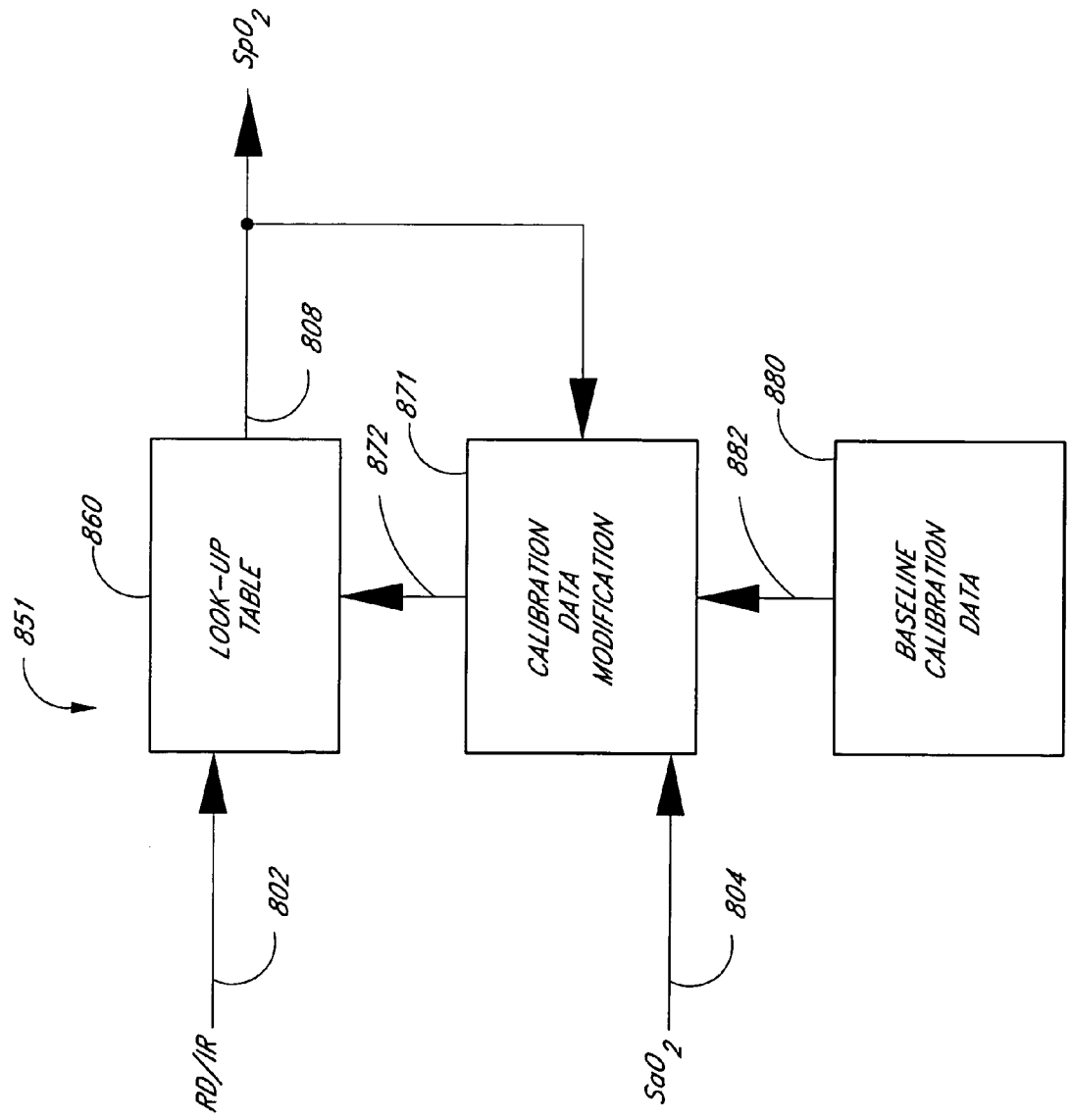
FIG. 8B is a functional block diagram of compensated pulse oximetry incorporating an $SaO_2$ parameter input and $SpO_2$ measurement feedback.
Figure 8C:
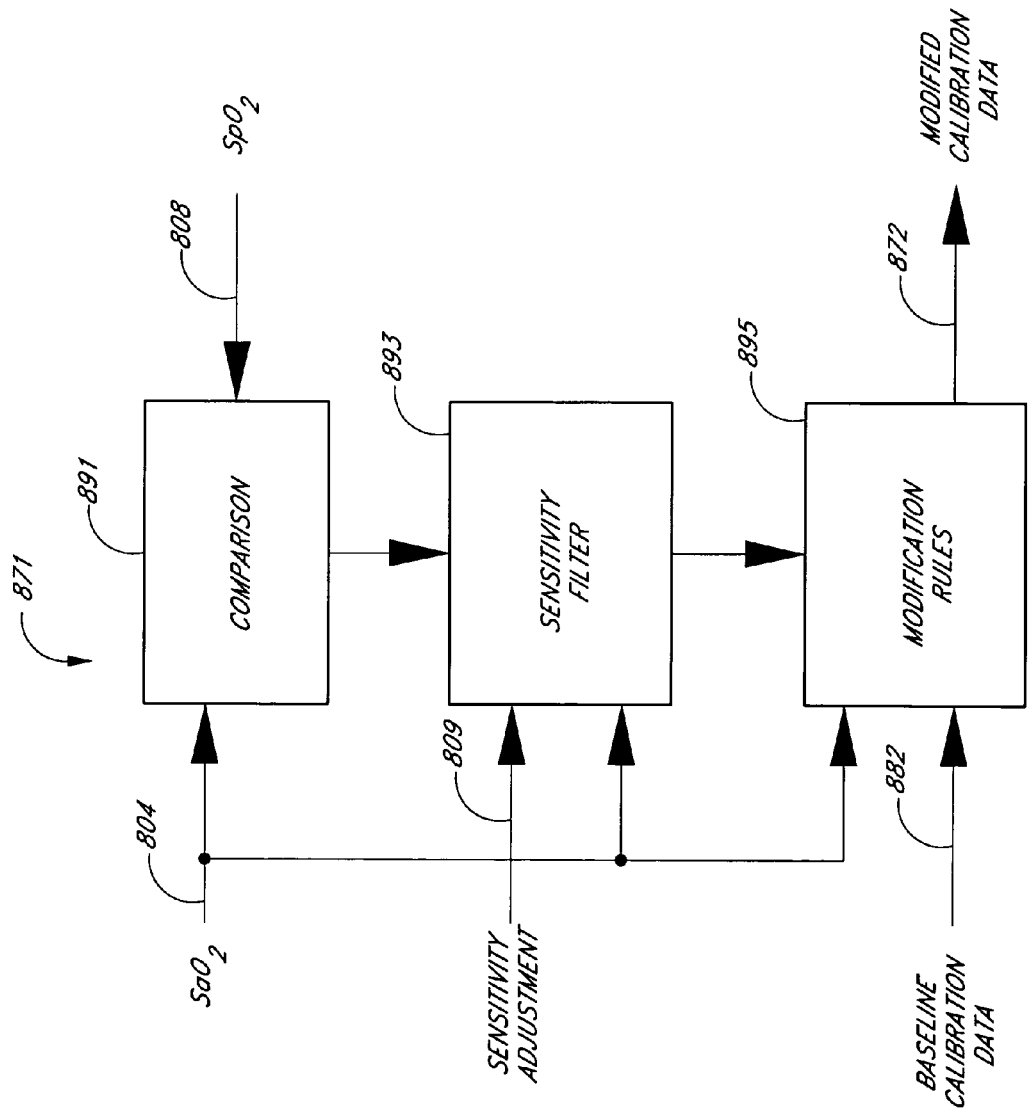
FIG. 8C is a functional block diagram of pulse oximetry calibration data modification.

FIGS. 8B–C describe one pulse oximeter embodiment of the compensation relationship 800 (FIG. 8A). As shown in FIG. 8B, the blood gas compensation relationship 851 has an RD/IR input 802 and generates an $SpO_2$ output 808 utilizing baseline calibration data 880 that is modified according to an input value of arterial oxygen saturation $SaO_2$. The compensation relationship 851 has a calibration data modification function 871 that provides modified calibration data 872 to a look-up table 860, as described with respect to FIG. 8A, above.

As shown in FIG. 8C, the calibration data modification 871 has comparison 891 and sensitivity filter 893 functions that input to modification rules 895 that operate on the baseline calibration data 882 to provide modified calibration data 872. The comparison 891 determines a difference between $SaO_2$ 804 and $SpO_2$ 808 so that the compensation relationship 871 can function to reduce the discrepancy between blood gas measurement and pulse oximeter measurements of oxygen saturation.

The responsiveness to blood gas measurements is determined by a sensitivity filter 893 and sensitivity adjustment 809. So as to reduce over-sensitivity of a calibration data to blood gas measurements, calibration data modification may require multiple blood gas input values over a range of saturation values and/or consistency within a tolerance range before calibration data is modified. Also, calibration data modification can be less sensitive to more frequently occurring normal saturation values and more sensitive to the less frequently occurring low saturation values. Hence, the sensitivity filter 893 may have a blood gas input 804 so that responsiveness varies with the range of blood gas sample values. Further, calibration data may be piecewise modified according to ranges of saturation values, so that an entire range of calibration data is not affected by blood gas measurements that are limited to a certain range of saturation values.

TABLE 1, below, illustrates one embodiment of the modification rules 895. Saturation Range is a range of blood gas measurements and a corresponding portion of the calibration curve to be replaced or modified. Number of Samples is the number of blood gas measurements required within the corresponding Saturation Range before a calibration curve modification or replacement is made. Sample Tolerance is the deviation allowed between measured $SpO_2$ and measured $SaO_2$ for a particular blood gas measurement to be considered. For example, the saturation ranges may be in 5% increments, i.e. 100–95%, 95–90%, etc. The number of samples may be, say, 4 for saturation measurements above 75% and 1 for saturation measurements below 75%. The sample tolerance may be $SpO_2-SaO_2=\pm 1\%$.

TABLE 1

Calibration Data Modification Rules

| SATURATION RANGE (%) | NUMBER OF SAMPLES | SAMPLE TOLERANCE |
|---|---|---|
| 100–$x_1$ | $n_1$ | $\Delta_1$ |
| $x_1$–$x_2$ | $n_2$ | $\Delta_2$ |
| . | . | . |
| . | . | . |
| . | . | . |
| $x_i$–50 | $n_i$ | $\Delta_i$ |

Depending on the embodiment, the modification rules 895 may operate on the baseline calibration data to select one of a family of calibration curves, determine the direction and amount of shift in a calibration curve, modify the shape of a calibration curve, rotate a calibration curve around a selected point on the curve, specify one or more points from which a calibration curve may be derived, or a combination of these actions. In this manner a pulse oximeter may be calibrated on site for individual patients, for improved accuracy as compared with total reliance on empirical calibration data derived from many individuals. Calibration curve modification in response to blood gas measurements is described in further detail with respect to FIGS. 9A–D, below.

FIGS. 9A–D illustrate calibration data modification utilizing a Bezier curve. In its most common form, a Bezier curve is a simple cubic equation defined by four points including the end points and two control points, as is well-known in the art. As shown in FIG. 9A a calibration curve 910, such as described with respect to FIG. 3, above can be approximated as a Bezier curve with an associated first control point 920 and second control point 930.

As shown in FIG. 9B, the initial Bezier curve 910 (FIG. 9A) can be modified in response to a blood gas measurement providing a first calibration point 940 at a relatively high saturation value. In particular, a modified calibration curve 911 can be derived in response to the first calibration point 940 by repositioning the first and second control points 920–930 so that the modified calibration curve 911 more closely approximates the first calibration point 940 than the original calibration curve 910 without significantly altering the original calibration curve 910 (FIG. 9A) within saturation ranges away from the first calibration point 940.

As shown in FIG. 9C, the modified calibration curve 911 (FIG. 9B) can be modified in response to a second calibration point 950 at a relatively low saturation value. In particular, a modified calibration curve 912 can be derived in response to the first and second calibration points 940–950 by again repositioning the first and second control points 920–930 so that the modified calibration curve 912 more closely approximates the calibration points 940–950.

As shown in FIG. 9D, the modified calibration curve 912 (FIG. 9C) can be modified yet again in response to a third calibration point 960. In particular, a modified calibration curve 913 can be derived in response to the three calibration points 940–960 by further repositioning the control points 920–930 so that the modified calibration curve 913 more closely approximates the calibration points 940–960.

Multiple calibration points may be accommodated by curve-fitting algorithms well-known in the art, such as a least-means-squared computation of the error between the modified calibration curve and the calibration points, as one example. Other polynomials curves may be used to derive modified calibration curves, and two or more sections of Bezier curves or other polynomial curves can be used to represent a modified calibration curve.

FIG. 10A illustrates a measurement correction compensation relationship 1000 having a look-up table 1010, calibration data 1020, and a measurement correction function 1030. The compensation relationship 1000 differs from the compensation relationship 800 (FIG. 8A) described above in that, an uncompensated physiological measurement 1018 is calculated and corrected to yield a compensated physiological measurement 1008. This contrasts with a compensated physiological measurement being directly derived from a spectral characteristic and parameters, as described with respect to FIG. 8A, above.

FIG. 10B illustrates an upgrade compensation relationship 1001 embodiment of the compensation relationship 1000 (FIG. 10A) described above. The compensation relationship 1001 advantageously upgrades the uncompensated oxygen saturation measurement of a conventional pulse oximeter. In particular, the look-up table 1010 and calibration curve 1020 may be as described with respect to FIGS. 2–3, above. In one embodiment, the measurement correction 1031 is a look-up table having a correction data set as input, where the correction data set is determined by statistical regression of experimental measurements obtained from human volunteers and calibrated measurements of oxygen saturation and associated parameters. In another embodiment, the measurement correction 1031 is a mathematical formula or algorithm that directly computes a compensated $SpO_2$ output from uncompensated $SpO_2$ and parameter inputs. In yet another embodiment, the measurement correction is a combination of look-up table and mathematical formula or algorithm. The compensation parameters may be, for example, one or more of T, pH, Hct, HbCO, MetHb, to name a few.

FIG. 11 illustrates a multidimensional calibration function 1100 having a look-up table 1110 and associated multidimensional calibration data 1120. The look-up table 1110 has a spectral characteristic input 1112, such as RD/IR, and one or more compensation parameters 1114, such as T, pH, Hct, HbCO, MetHb, etc., as described with respect to FIG. 7, above. In response to the spectral characteristic 1112 and parameter 1114 inputs, the look-up table 1110 provides a physiological measurement output 1118, such as a compensated oxygen saturation value, also as described with respect to FIG. 7, above. The look-up table 1110 may function as a calibration surface 1210 (FIG. 12) in a somewhat analogous manner to the calibration curve described with respect to FIG. 3, above. The multidimensional calibration data 1120 may be determined by statistical regression of experimental measurements obtained from human volunteers and calibrated measurements of the physiological measurement and associated parameters. Also, the look-up table 1110 and calibration data 1120 may be replaced by or combined with a mathematical formula or algorithm, theoretically or experimentally derived, used to directly compute a physiological measurement from spectral characteristic and parameter inputs.

FIG. 12 is a three-dimensional graph 1200 illustrating the look-up table calibration function described with respect to FIG. 11, above. The graph 1200 has an x-axis 1201 representing derived spectral characteristic values, a y-axis 1203 representing a parameter value, and a z-axis 1205 representing physiological measurement values that result from locating a position on the surface 1210 corresponding to a combination of spectral characteristic and parameter values. The three-dimensional graph 1200 may be extended to accommodate multiple parameters, so as to create a calibration surface in multidimensional hyperspace.

In one advantageous embodiment, a blood gas measurement of HbCO and/or MetHb is manually entered into a pulse oximeter and utilized to generate a compensated value of $SpO_2$. As described above, conventional pulse oximetry utilizes two wavelengths, assuming that Hb and $HbO_2$ are the only significant absorbers. However, HbCO and MetHb may also be significant absorbers at RD and IR wavelengths. The presence of significant concentrations of HbCO and MetHb have different effects on a conventional pulse oximeter estimate of oxygen saturation. $HbO_2$ and HbCO have similar extinctions at the RD wavelength, as do MetHb and Hb. At the IR wavelength, HbCO is relatively transparent whereas MetHb has greater extinction than the other hemoglobins. The two wavelength assumption tends to lump $HbO_2$ and HbCO together, i.e. HbCO is counted as an oxygen carrying form of hemoglobin, causing a conventional pulse oximeter to overestimate oxygen saturation. As MetHb increases, RD/IR tends to unity and $SpO_2$ tends to a constant (e.g. 85%) regardless of oxygen saturation. A manually entered value of HbCO and or MetHb is used as a parameter in conjunction with the functions described above with respect to any of FIGS. 7–11, so as to distinguish these hemoglobin species from $HbO_2$ and Hb, providing a more accurate, HbCO and/or MetHb compensated, value of $SpO_2$.

FIG. 13A illustrates a wavelength compensation relationship 1300 having a look-up table 1310, wavelength-dependent calibration data 1320, and a wavelength determination function 1330. The wavelength compensation relationship 1300 advantageously changes sensor wavelength to generate a wavelength-compensated physiological measurement output 1308. The look-up table 1310 has a spectral characteristic input 1302 and generates a physiological measurement output 1308 utilizing the wavelength-dependent calibration data 1320. The wavelength determination function 1330 has parameter 1304 inputs and, in one embodiment, a feedback input of the physiological measurement 1308, and provides a sensor wavelength selection output 1338. The wavelength selection output 1338 provides a calibration data 1320 input for selecting wavelength-dependent portions of the calibration data 1320. As above, the look-up table 1310 and/or the calibration data 1320 may be replaced by or combined with mathematical formulas or algorithms. The wavelength control output 1338 is a feedback path to a controller 669 (FIG. 6) and/or drivers 662 (FIG. 6), for example, so as to modify the wavelength of a multiple-wavelength sensor 610 (FIG. 6). FIG. 13B, below, illustrates one advantageous pulse oximeter embodiment of the wavelength compensation relationship 1300.

FIG. 13B illustrates an oxygen saturation dependent wavelength compensation relationship 1301 having a null parameter input 1304 (FIG. 13A), i.e. no parameter is used, and a wavelength control output 1338 that is dependent on the $SpO_2$ output 1308. In particular, the wavelength determination function 1330 has $SpO_2$ 1308 as input and generates a wavelength selection output 1338, accordingly. For example, the wavelength selection output 1338 determines particular red and IR wavelengths to be used for conventional pulse oximetry measurements and a corresponding one of a family of wavelength dependent calibration curves 1320. In this manner, sensor wavelength can be dynamically adjusted based upon saturation levels, e.g. a first red and/or IR wavelength may be used in low saturation conditions and a second red and/or IR wavelength may be used in normal saturation conditions.

FIG. 14 illustrates parameter compensation of pulse rate measurements. In this pulse oximetry embodiment, the compensation relationship 1400 includes a pulse rate calculation 1410 having a plethysmograph input 1402 and providing a pulse rate measurement output 1408. The pulse rate calculation 1410 also has one or more parameter inputs 1404, such as a manual input indicating the presence of an implant device, such as an IABP or a pacemaker, or the presence of an arrhythmia. The parameter input is used to alter the pulse rate calculation 1410 so as to derive a more accurate pulse rate measurement 1408. For example, the criteria for determining a physiologically acceptable pulse on the plethysmograph input 1402, such as aspects of the pulse shape, may be altered according to the parameter input 1404. Pulse rate calculations are described in U.S. Pat. No. 6,463,311 entitled "Plethysmograph Pulse Recognition Processor," which is assigned to Masimo Corporation, Irvine, Calif. and incorporated by reference herein.

A parameter compensated physiological monitor has been disclosed in detail in connection with various embodiments. These embodiments are disclosed by way of examples only and are not to limit the scope of the claims that follow. One of ordinary skill in the art will appreciate many variations and modifications.

What is claimed is:

1. A monitor comprising:
   a primary input from which a spectral characteristic of a tissue site is derivable;
   a secondary input from which at least one parameter is determinable; and
   a processor configured to output a compensated physiological measurement in response to said primary input and said secondary input utilizing a compensation relationship between said spectral characteristic and said at least one parameter and said compensated physiological measurement;
   wherein said compensation relationship comprises:
      baseline calibration data relating said spectral characteristic to an uncompensated physiological measurement;
      modified calibration data generated from a modification of said baseline calibration data in response to said at least one parameter; and
      a look-up table having sold spectral characteristic as an input and providing said compensated physiological measurement as an output according to said calibration data;
   wherein said at least one parameter is a blood gas measurement and said compensation relationship further comprises:
      a comparison of said uncompensated physiological measurement with said blood gas measurement;
      a sensitivity control; and
      modification rules responsive to said comparison and said sensitivity control, said modification rules determining said modification.

2. The monitor according to claim 1 wherein said modification rules include at least one polynomial function approximating at least a section of said baseline calibration data and adjustable so as to accommodate said blood gas measurement.

3. The monitor according to claim 2 wherein said at least one polynomial function can be represented as a Bezier curve.

4. A monitor comprising:
   a primary input from which a spectral characteristic of a tissue site is derivable;
   a secondary input from which at least one parameter is determinable wherein said spectral characteristic has a dependence on said parameter; and
   a processor configured to output a compensated physiological measurement in response to a primary input and said secondary input utilizing a relationship between said spectral characteristic and said at least one parameter and said compensated physiological measurement;
   wherein said compensation relationship comprises:
      calibration data relating said spectral characteristic to an uncompensated physiological measurement;
      a look-up table having at least said spectral characteristic and said at least one parameter as an input and providing said compensated measurement as an output according to said calibration data; and wherein said at least one parameter is a carboxyhemoglobin concentration and said look up table distinguishes carboxyhemoglobin from oxyhemoglobin.

5. A monitor comprising:
a primary input from which a spectral characteristic of a tissue site is derivable;
a secondary input from which at least one parameter is determinable wherein said spectral characteristic has a dependence on said parameter; and
a processor configured to output a compensated physiological measurement in response to said primary input and said secondary input utilizing a relationship between said spectral characteristic and said at least one parameter and said compensated physiological measurement;
wherein said compensation relationship comprises:
calibration data representing a plurality of wavelength-dependent compensation calibration curves, each of said compensation calibration curves relating said spectral characteristic to said compensated physiological measurement;
a look-up table having said spectral characteristic as an input and providing as an output said compensated physiological measurement according to said compensation calibration curves; and
a wavelength determination in response to said at least one parameter so as to select a sensor wavelength and a corresponding one of said compensation calibration curves.

6. A monitoring method comprising the steps of:
inputting a sensor signal responsive to a spectral characteristic of a tissue site;
deriving a physiological measurement from said characteristic;
obtaining a parameter, wherein said physiological measurement has a dependency on said parameter;
determining a relationship between said spectral characteristic and said parameter that accounts for said dependency;
compensating said physiological measurement for said parameter utilizing said relationship; and
displaying said physiological measurement;
wherein said compensating step comprises the substeps of:
storing baseline calibration data;
modifying said baseline calibration data according to said parameter so as to provide modified calibration data; and
looking-up said physiological measurement from said modified calibration data according to said spectral characteristic; and
wherein said physiological measurement provides an SpO$_2$ value and said parameter is a manually input SaO$_2$ value, said modifying substep comprising the further steps of:
comparing said SpO$_2$ value to said SaO$_2$ value so as to determine a difference; and
determining said modified calibration data so as to reduce said difference.

7. A monitoring method comprising the steps of:
inputting a sensor signal responsive to a spectral characteristic of a tissue site;
deriving a physiological measurement from said characteristic;
obtaining a parameter, wherein said physiological measurement has a dependency on said parameter;
determining a relationship between said spectral characteristic and said parameter that accounts for said dependency;
compensating said physiological measurement for said parameter utilizing said relationship; and
displaying said physiological measurement;
wherein said compensating step comprises the substeps of:
storing baseline calibration data;
looking-up said compensated physiological measurement from said calibration data according to said spectral characteristic and said parameter; and
wherein said parameter is a hemoglobin constituent measurement and said looking-up comprises the substeps of:
distinguishing said hemoglobin constituent from oxyhemoglobin and reduced hemoglobin; and
providing an adjusted oxygen saturation measurement according to said distinguishing substep.

8. A monitoring method comprising the steps of;
inputting a sensor signal responsive to a spectral characteristic of a tissue site;
deriving a physiological measurement from said characteristic;
obtaining a parameter, wherein said physiological measurement has a dependency on said parameter;
determining a relationship between said spectral characteristic and said parameter that accounts for said dependency;
compensating said physiological measurement for said parameter utilizing said relationship;
wherein said compensating step comprises the substeps of:
storing wavelength-dependent calibration data;
determining a wavelength according to at least one of said parameter and said physiological measurement;
selecting an active portion of said calibration data according to said wavelength;
adjusting a sensor so that said spectral characteristic corresponds to said wavelength;
looking-up said physiological measurement from said active portion of said calibration data according to said spectral characteristic; and
displaying said physiological measurement.

9. The monitoring method according to claim 8 wherein said parameter is a null value and said determining substep comprises the substeps of:
identifying a range of said physiological measurement; and
specifying said wavelength according to said range.

10. The monitoring method according to claim 9 wherein said physiological measurement corresponds to oxygen saturation at said tissue site and said wavelength has a first value at normal oxygen saturation levels and a second value at below normal oxygen saturation levels.

11. A monitor comprising:
a primary input means for determining a spectral characteristic associated with a tissue site;
a secondary input means for determining a parameter that is relevant to measuring oxygen saturation at said tissue site; and a compensation relationship means for relating said spectral characteristic, said parameter and an oxygen saturation measurement;

wherein said compensation relationship comprises a means for modifying a sensor wavelength and for selecting corresponding wavelength dependent calibration data.

12. A monitor comprising:

a primary input from which a spectral characteristic of a tissue site is derivable;

a secondary input from which at least one parameter is determinable; and a processor configured to output a compensated physiological measurement in response to said primary input and said secondary input utilizing a relationship between said spectral characteristic and said at least one parameter and said compensated physiological measurement;

wherein said compensation relationship comprises a sensitivity control.

13. A monitoring method comprising the steps of;

receiving a sensor signal responsive to a physiological parameter of a tissue site;

deriving a physiological indication of said physiological parameter;

obtaining a parameter indication, wherein said physiological indication has a dependency on said parameter indication;

determining a relationship between said physiological indication and said parameter indication that accounts for said dependency;

determining a measurement of said physiological parameter utilizing said relationship;

wherein said relationship comprises a sensitivity control; and displaying said measurements.

* * * * *